United States Patent
Mizumoto et al.

(10) Patent No.: US 9,075,043 B2
(45) Date of Patent: *Jul. 7, 2015

(54) SAMPLE ANALYZER, SAMPLE INFORMATION PROCESSING APPARATUS, AND SAMPLE ANALYSIS METHOD

(71) Applicants: Toru Mizumoto, Kobe (JP); Fumio Inoue, Akashi (JP)

(72) Inventors: Toru Mizumoto, Kobe (JP); Fumio Inoue, Akashi (JP)

(73) Assignee: SYSMEX CORPORATION, Hyogo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/035,541

(22) Filed: Sep. 24, 2013

(65) Prior Publication Data

US 2014/0024072 A1 Jan. 23, 2014

Related U.S. Application Data

(63) Continuation of application No. PCT/JP2012/057459, filed on Mar. 23, 2012.

(30) Foreign Application Priority Data

Mar. 24, 2011 (JP) ................................. 2011-065537

(51) Int. Cl.
*G01N 33/493* (2006.01)
*G01N 35/00* (2006.01)
*G01N 33/50* (2006.01)

(52) U.S. Cl.
CPC .............. *G01N 33/50* (2013.01); *G01N 33/493* (2013.01); *G01N 35/00613* (2013.01); *G01N 35/00603* (2013.01)

(58) Field of Classification Search
None
See application file for complete search history.

(56) References Cited

U.S. PATENT DOCUMENTS

| 5,851,487 A | 12/1998 | Katayama et al. |
| 2007/0072301 A1 | 3/2007 | Fukuda et al. |
| 2007/0072321 A1 | 3/2007 | Sherrer et al. |
| 2008/0028871 A1 | 2/2008 | Kitaoka |
| 2010/0300217 A1* | 12/2010 | Mizumoto ................. 73/863.01 |

FOREIGN PATENT DOCUMENTS

| JP | 06-102272 A | 4/1994 |
| JP | 06-138120 A | 5/1994 |
| JP | 09-218197 A | 8/1997 |
| JP | 2000-310643 A | 11/2000 |
| JP | 2002-323501 A | 11/2002 |
| JP | 2005-315830 A | 11/2005 |
| JP | 2006-098219 A | 4/2006 |
| JP | 2008-039556 A | 2/2008 |
| JP | 2010-175395 A | 8/2010 |
| JP | 2010-210328 A | 9/2010 |

OTHER PUBLICATIONS

Thongboonkerd, V. 2007. Practical Points in Urinary Proteomics. Journal of Proteome Research 6:3881-3890. specif. p. 3883.*
Simerville, J.A. et al. 2005. Urinalysis: A comprehensive review. American Family Physician 71(6):1153-1162. specif. p. 1153.*
International Search Report of PCT/JP2012/057459 dated Apr. 24, 2012.

* cited by examiner

*Primary Examiner* — John S Brusca
*Assistant Examiner* — Sharon M Papciak
(74) *Attorney, Agent, or Firm* — Sughrue Mion, PLLC

(57) ABSTRACT

A sample analyzer includes: a first measurement part which performs measurement on a sample for a first measurement item; a second measurement part which performs a measurement on the sample for a second measurement item; an output section; and a controller configured to control the output section to output, when a time difference between a measurement on a sample performed by the first measurement part and a measurement on the sample performed by the second measurement part exceeds a predetermined time period, information based on an excess of the time difference.

22 Claims, 16 Drawing Sheets

FIG. 4A

QUALITATIVE MEASUREMENT DB

| No. | SAMPLE NUMBER | MEASUREMENT DATE | MEASUREMENT TIME | MEASUREMENT RESULT | | |
|---|---|---|---|---|---|---|
| | | | | GLU | PRO | ... |
| 36 | 0322000089 | 2010/08/10 | 11:38:34 | ... | ... | ... |
| 35 | 0322000091 | 2010/08/10 | 11:34:12 | ... | ... | ... |
| 34 | 0322000093 | 2010/08/10 | 11:32:47 | ... | ... | ... |
| 33 | 0322000092 | 2010/08/10 | 11:31:12 | ... | ... | ... |
| 32 | 0322000091 | 2010/08/10 | 11:30:37 | ... | ... | ... |
| 31 | 0322000090 | 2010/08/10 | 10:33:12 | ... | ... | ... |
| 30 | 0322000089 | 2010/08/10 | 10:32:54 | ... | ... | ... |
| 29 | 0322000088 | 2010/08/10 | 10:32:36 | ... | ... | ... |
| 28 | 0322000087 | 2010/08/10 | 10:32:18 | ... | ... | ... |
| 27 | 0322000086 | 2010/08/10 | 10:32:00 | ... | ... | ... |
| ... | ... | ... | ... | ... | ... | ... |

FIG. 4B

SEDIMENT MEASUREMENT DB

| No. | SAMPLE NUMBER | MEASUREMENT DATE | MEASUREMENT TIME | MEASUREMENT RESULT | | |
|---|---|---|---|---|---|---|
| | | | | RBC | WBC | ... |
| 40 | 0322000097 | 2010/08/10 | 13:01:48 | ... | ... | ... |
| 39 | 0322000096 | 2010/08/10 | 13:01:12 | ... | ... | ... |
| 38 | 0322000095 | 2010/08/10 | 13:00:36 | ... | ... | ... |
| 37 | 0322000094 | 2010/08/10 | 13:00:00 | ... | ... | ... |
| 36 | 0322000091 | 2010/08/10 | 11:31:02 | ... | ... | ... |
| 35 | 0322000090 | 2010/08/10 | 11:12:45 | ... | ... | ... |
| 34 | 0322000089 | 2010/08/10 | 10:45:38 | ... | ... | ... |
| 33 | 0322000088 | 2010/08/10 | 10:33:10 | ... | ... | ... |
| 32 | 0322000087 | 2010/08/10 | 10:32:46 | ... | ... | ... |
| 31 | 0322000086 | 2010/08/10 | 10:32:10 | ... | ... | ... |
| ... | ... | ... | ... | ... | ... | ... |

FIG.5A

MERGED DB

| No. | MEASUREMENT DATE | MEASUREMENT TIME | QUALITATIVE No. | SEDIMENT No. | CROSS-CHECK RESULT | | | | | | | | | | MEASUREMENT ELAPSED TIME | RELIABILITY |
|---|---|---|---|---|---|---|---|---|---|---|---|---|---|---|---|---|
| | | | | | 1 | 2 | 3 | 4 | 5 | 6 | 7 | 8 | 9 | 10 | | |
| 31 | 2010/08/10 | 11:38:34 | 36 | 34 | 0 | 0 | 0 | 0 | 0 | 0 | 0 | 0 | 0 | 0 | 52:56 | 1 |
| 30 | 2010/08/10 | 11:34:12 | 35 | 36 | 1 | 0 | 0 | 0 | 0 | 0 | 0 | 0 | 0 | 0 | 3:10 | 0 |
| 29 | 2010/08/10 | 11:32:57 | 34 | 0 | 0 | 0 | 0 | 0 | 0 | 0 | 0 | 0 | 0 | 0 | 0 | 0 |
| 28 | 2010/08/10 | 11:31:22 | 33 | 0 | 0 | 0 | 0 | 0 | 0 | 0 | 0 | 0 | 0 | 0 | 0 | 0 |
| 27 | 2010/08/10 | 11:31:02 | 32 | 36 | 1 | 0 | 0 | 0 | 0 | 0 | 0 | 0 | 0 | 0 | 0:25 | 0 |
| 26 | 2010/08/10 | 11:12:45 | 31 | 35 | 0 | 0 | 0 | 0 | 0 | 0 | 0 | 0 | 0 | 0 | 39:33 | 1 |
| 25 | 2010/08/10 | 10:45:38 | 30 | 34 | 5 | 0 | 0 | 0 | 0 | 0 | 0 | 0 | 0 | 0 | 12:44 | 0 |
| 24 | 2010/08/10 | 10:33:10 | 29 | 33 | 1 | 3 | 0 | 0 | 0 | 0 | 0 | 0 | 0 | 0 | 0:34 | 0 |
| 23 | 2010/08/10 | 10:32:46 | 28 | 32 | 2 | 4 | 0 | 0 | 0 | 0 | 0 | 0 | 0 | 0 | 0:28 | 0 |
| 22 | 2010/08/10 | 10:32:10 | 27 | 31 | 3 | 0 | 0 | 0 | 0 | 0 | 0 | 0 | 0 | 0 | 0:10 | 0 |
| ⋮ | ⋮ | ⋮ | ⋮ | ⋮ | ⋮ | ⋮ | ⋮ | ⋮ | ⋮ | ⋮ | ⋮ | ⋮ | ⋮ | ⋮ | ⋮ | ⋮ |

FIG.5B

CROSS-CHECK TABLE

| No. | TARGET | DETAIL |
|---|---|---|
| 1 | BLD x RBC | ⋯ |
| 2 | LEU x WBC | ⋯ |
| 3 | PRO x CAST | ⋯ |
| 4 | NIT x BACT | ⋯ |
| ⋮ | ⋮ | ⋮ |

FIG.5C

□ ERROR
□ NORMAL (Grid plot: PRO (vertical axis, 1–9) vs CAST (horizontal axis, 1–9))

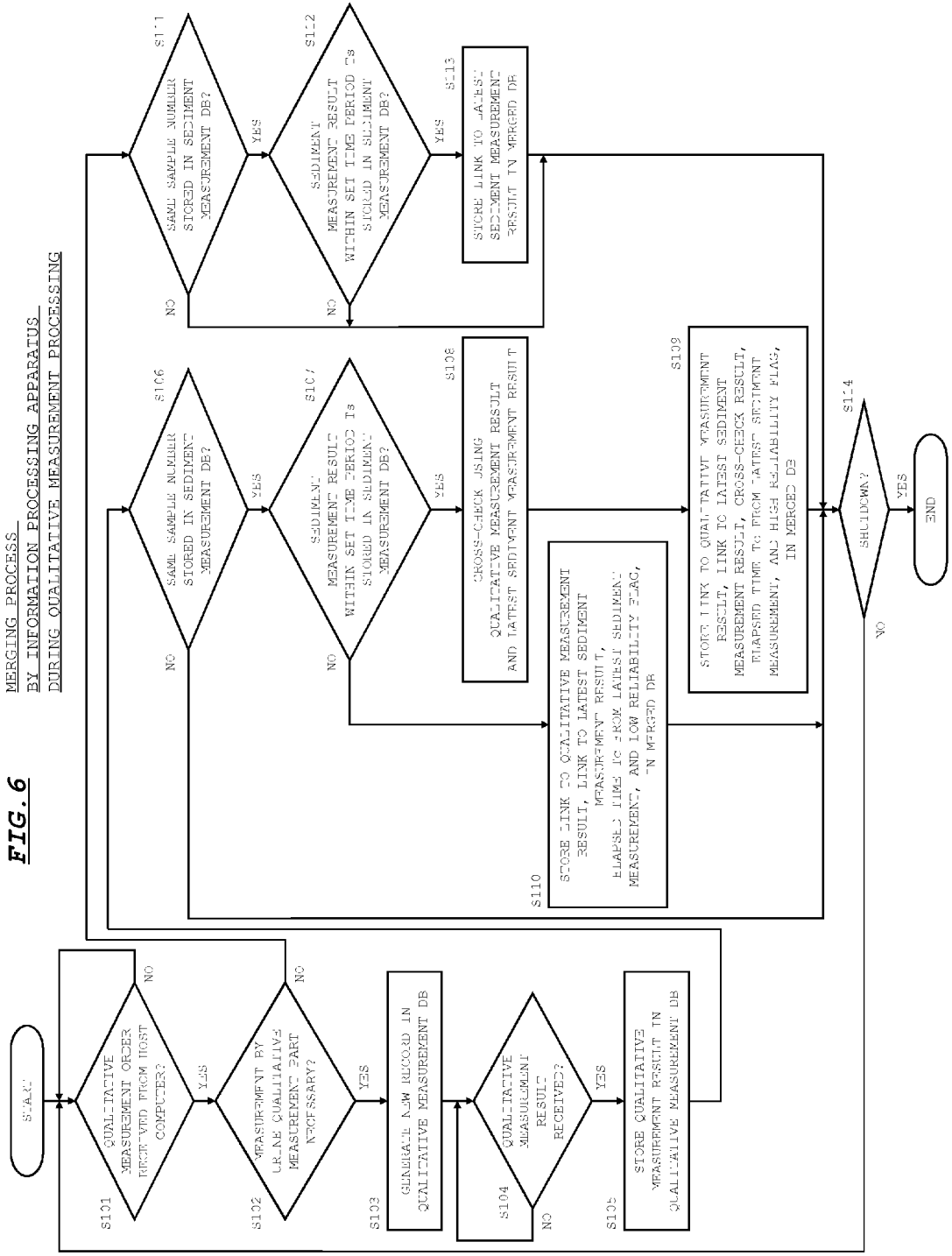

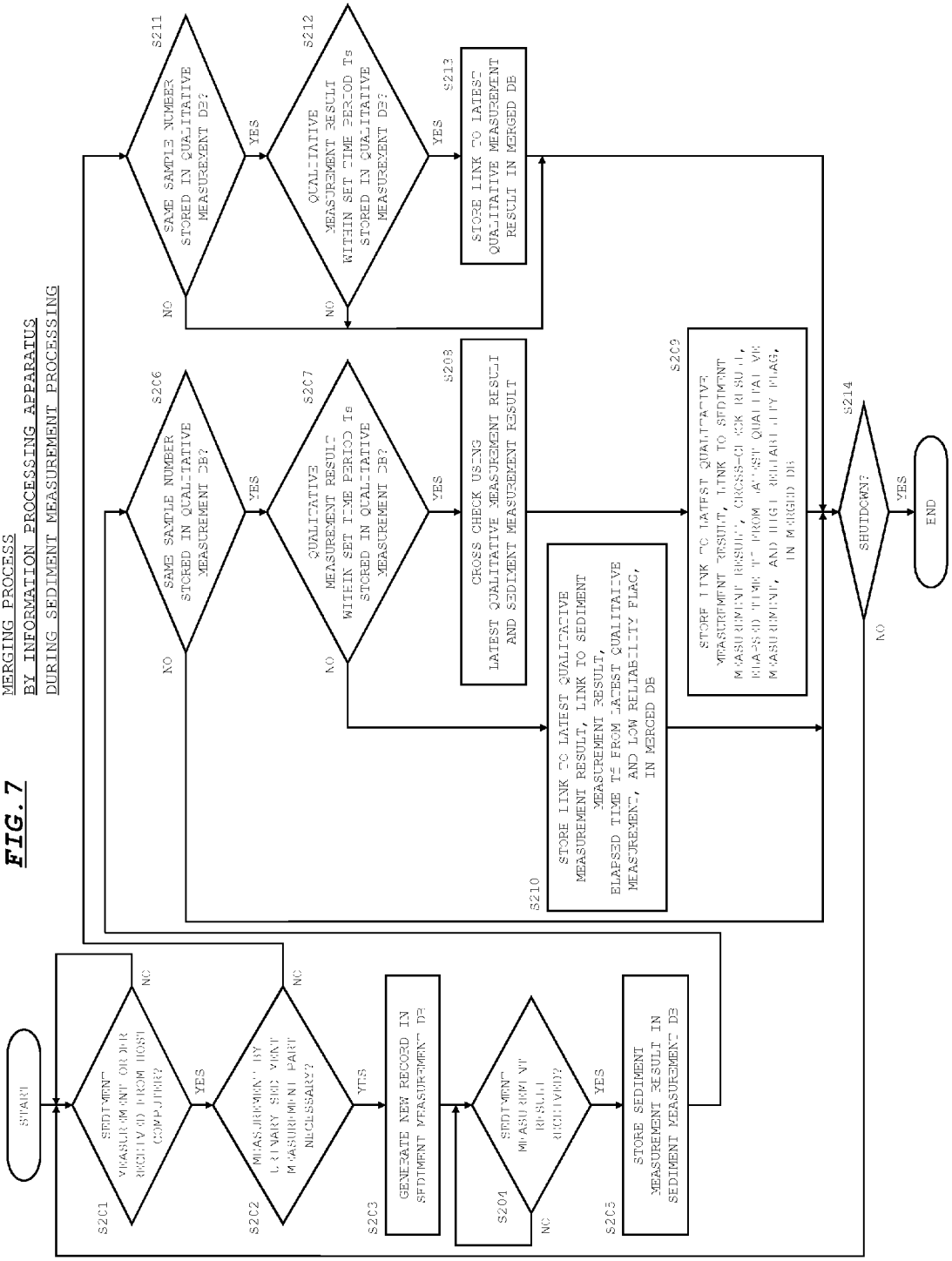

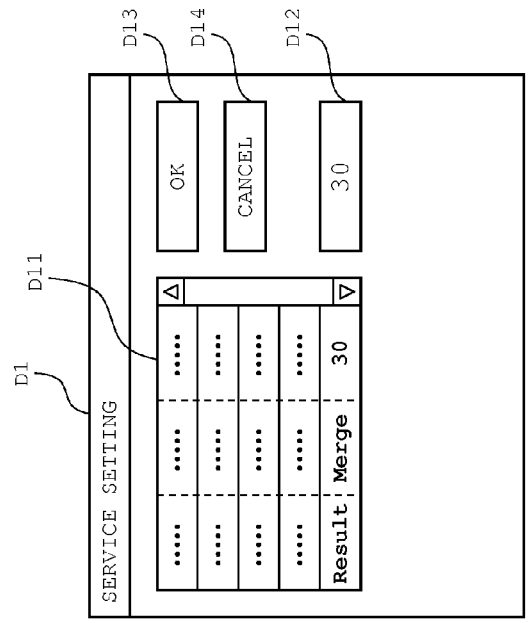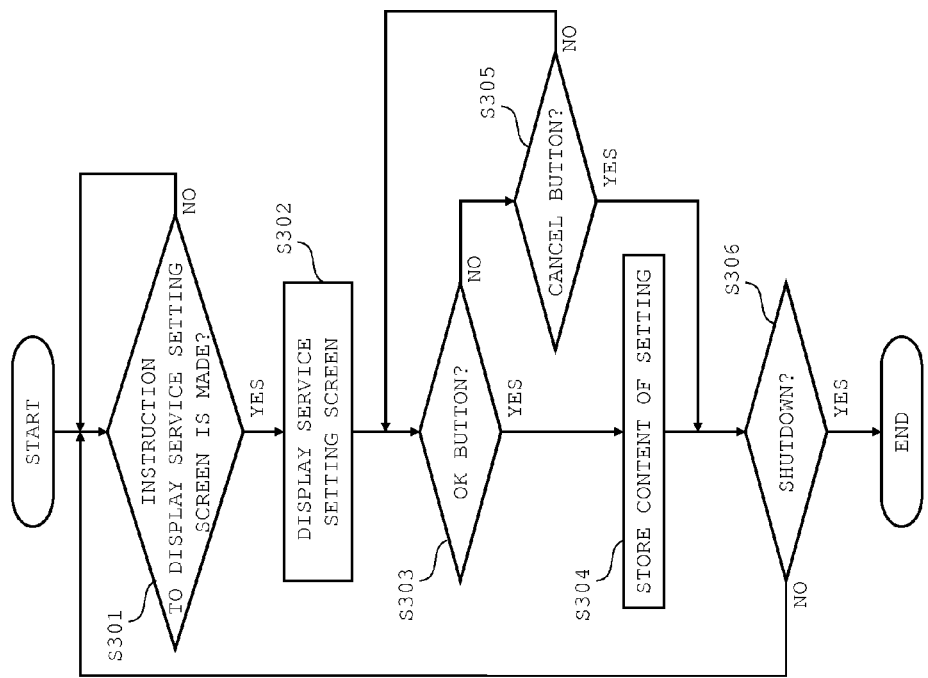

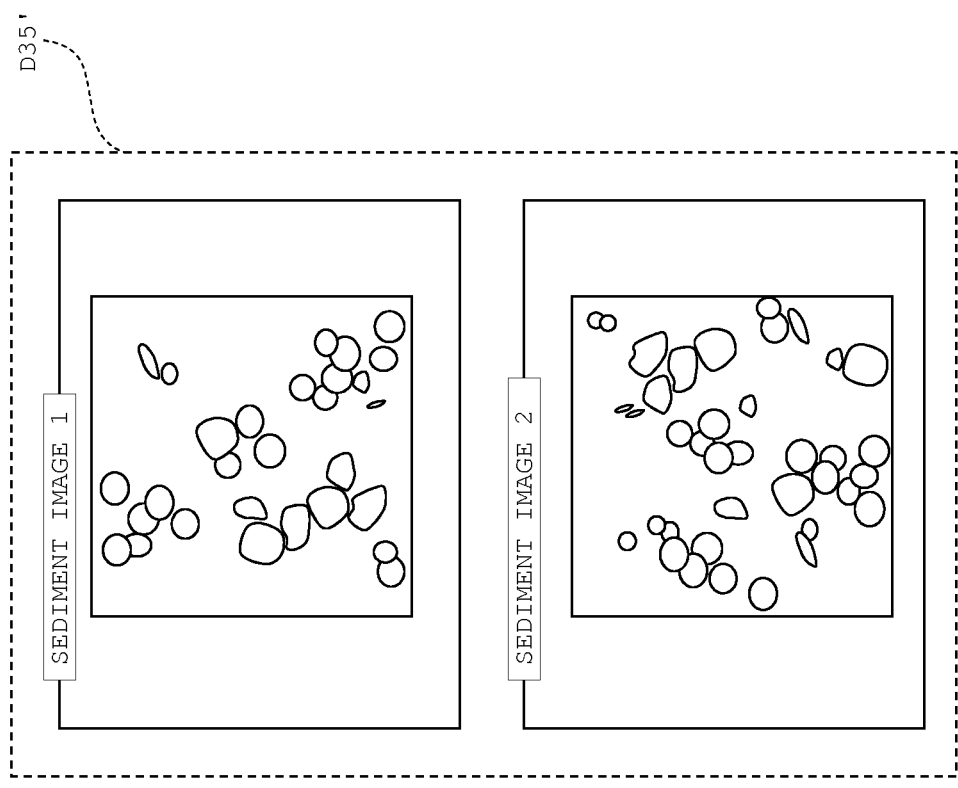

US 9,075,043 B2

SAMPLE ANALYZER, SAMPLE INFORMATION PROCESSING APPARATUS, AND SAMPLE ANALYSIS METHOD

CROSS REFERENCE TO RELATED APPLICATION

This application is a continuation of International Application No. PCT/JP2012/057459 filed on Mar. 23, 2012, entitled "SAMPLE ANALYZER, SAMPLE INFORMATION PROCESSING APPARATUS, AND SAMPLE ANALYSIS METHOD", which claims priority under 35 U.S.C. Section 119 of Japanese Patent Applications No. 2011-065537 filed on Mar. 24, 2011, entitled "SAMPLE ANALYZER, SAMPLE INFORMATION PROCESSING APPARATUS, AND SAMPLE ANALYSIS METHOD". The disclosure of the above applications are incorporated herein by reference.

BACKGROUND OF THE INVENTION

1. Field of the Invention

The present invention relates to a sample analyzer, a sample information processing apparatus, and a sample analysis method for performing measurement and analysis of samples.

2. Disclosure of Related Art

In sample analysis, there are cases where measurement and analysis are performed on the same sample a plurality of times. In such cases, measurement items may be different or the same in each measurement and analysis.

For example, in a test of a urine sample, a qualitative measurement and a sediment measurement are often performed. A urine qualitative measurement is a measurement method for obtaining a negative/positive result for each measurement item, based on the color of a reaction test piece for the measurement item when a test strip having the test piece attached thereto is immersed in a subject urine specimen. A urinary sediment measurement is a measurement method for classifying and counting formed elements in a subject urine specimen. Urine analyzers for automatizing such urine tests are known (For example, U.S. Patent Application Publication No. 2007/072321 and U.S. Pat. No. 5,851,487). In these cases, for example, a urinary sediment measurement is performed, based on a urine qualitative measurement result. Other than this, there may be a case where after a urine qualitative measurement has been performed, a urine qualitative measurement is performed again, or a case where after a urinary sediment measurement has been performed, a urinary sediment measurement is performed again.

Further, in analysis of a blood sample, there are cases where retesting of the same sample is performed under a predetermined condition. In such a case, retesting is performed for the same measurement items as those at the time of the initial test, or retesting is performed for high spec measurement items different from the measurement items at the time of the initial test. In addition to this, in analysis of a blood sample, there are cases where measurement and analysis are performed for each of biochemical measurement items and immunological measurement items.

In a case where measurement and analysis are performed on the same sample a plurality of times, a time difference will exist between measurements. In general, the longer this time difference is, the less reliable a measurement result obtained in a later measurement becomes. For example, after a urine qualitative measurement was performed, if a temporary trouble has occurred in the apparatus for the urinary sediment measurement, or if it has become necessary to replace a reagent, a urinary sediment measurement is performed after a long time period has elapsed since the urine qualitative measurement was performed. In such a case, there is a risk of bacteria having increased in the urine sample, and thus, the reliability of the urinary sediment measurement result is reduced.

SUMMARY OF THE INVENTION

A first aspect of the present invention relates to a sample analyzer. The sample analyzer according to this aspect includes: a first measurement part which performs a measurement on a sample for a first measurement item;

a second measurement part which performs a measurement on the sample for a second measurement item;

an output section; and a controller configured to control the output section to output, when a time difference between a measurement on a sample performed by the first measurement part and a measurement on the sample performed by the second measurement part exceeds a predetermined time period, information based on an excess of the time difference.

A second aspect of the present invention relates to a sample information processing apparatus connected to a first measurement part which performs a measurement on a sample for a first measurement item and a second measurement part which performs a measurement on the sample for a second measurement item. The sample information processing apparatus according to this aspect includes:

an output section; and a controller configured to control the output section to output, when a time difference between a measurement on a sample performed by the first measurement part and a measurement on the sample performed by the second measurement part exceeds a predetermined time period, information based on an excess of the time difference.

A third aspect of the present invention relates to a sample analysis method for performing a measurement and an analysis of a sample. The sample analysis method according to this aspect includes steps of:

performing a first measurement on a sample for a first measurement item;

performing a second measurement on the sample for a second measurement item; and outputting, when a time difference between the first measurement on a sample and the second measurement on the sample exceeds a predetermined time period, information based on an excess of the time difference.

BRIEF DESCRIPTION OF THE DRAWINGS

The above and other objects and new features of the present invention will be fully clarified by the following description of the embodiment, when read in conjunction with accompanying drawings.

FIGS. 4A and 4B respectively illustrate a concept of a configuration of a qualitative measurement DB and a concept of a configuration of a sediment measurement DB according to an embodiment;

FIG. 5A illustrates a concept of a configuration of a merged DB and FIGS. 5B and 5C illustrate a concept of a configuration of a cross-check table according to an embodiment;

FIG. 6 is a flow chart showing a merging process performed by an information processing apparatus during qualitative measurement processing according to an embodiment;

FIG. 7 is a flow chart showing a merging process performed by an information processing apparatus during sediment measurement processing according to an embodiment;

FIG. 9A is a flow chart showing a setting process performed by an information processing apparatus and FIG. 9B shows a service setting screen according to an embodiment;

FIG. 13 shows a merged data displaying screen when it has been determined that the reliability of a sediment measurement result is low according to an embodiment;

FIG. 14 shows a merged data displaying screen when it has been determined that the reliability of a qualitative measurement result is low according to an embodiment;

FIG. 15 shows a modification of a merged data displaying screen when it has been determined that the reliability of a sediment measurement result is low according to an embodiment; and FIG. 16 shows a modification of a sediment measurement result displaying region in a merged data displaying screen according to an embodiment.

Figure 1:
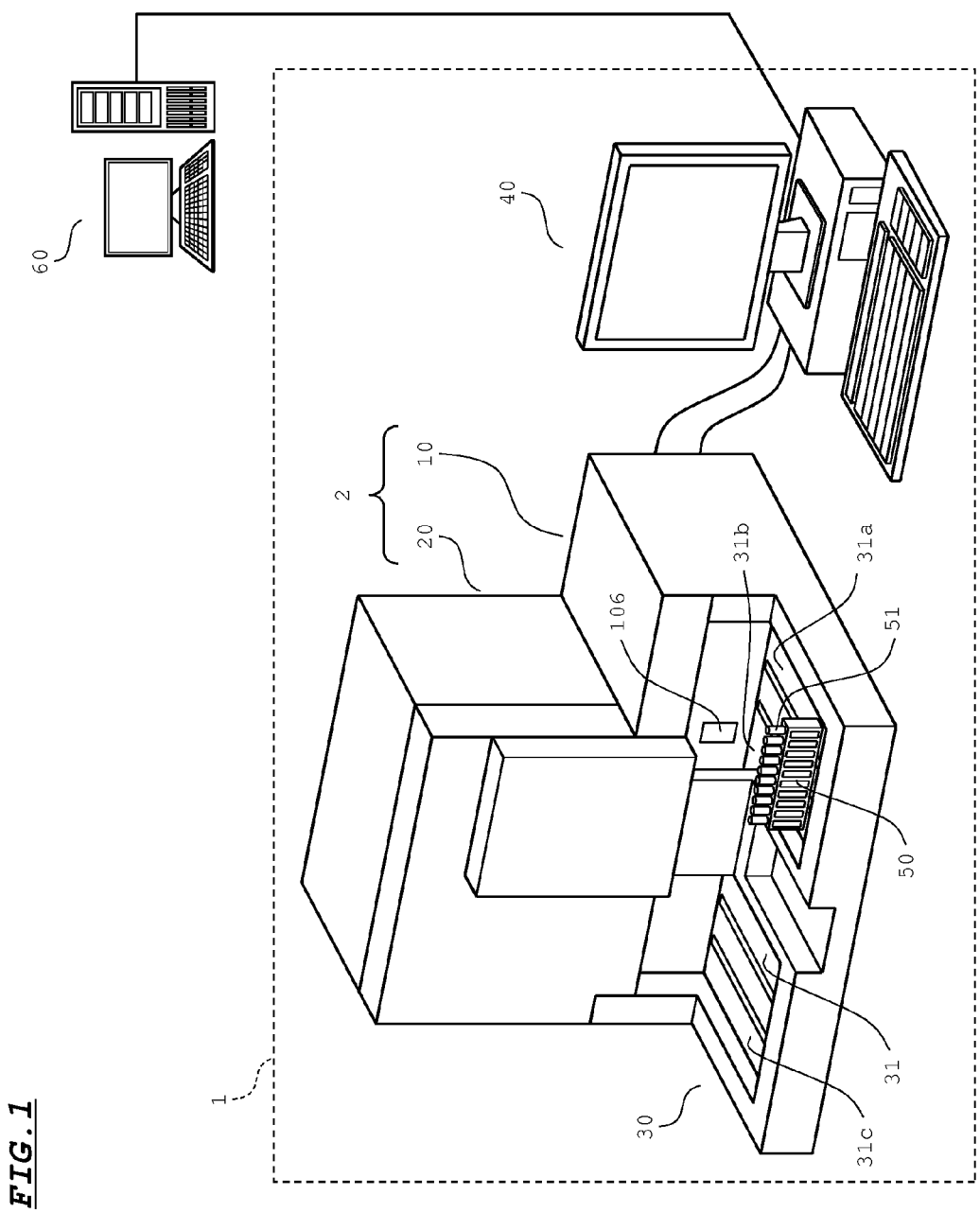
FIG. 1 shows an overall configuration of a system including a urine analyzer according to an embodiment.

It should be noted that the drawings are solely for description and do not limit the scope of the present invention by any degree.

DESCRIPTION OF THE PREFERRED EMBODIMENTS

The present embodiment is realized by applying the present invention to a clinical sample analyzer which performs tests (urine qualitative test) regarding urine protein, urine sugar, and the like, and tests (urinary sediment test) regarding red blood cells, white blood cells, epithelial cells, and the like contained in urine. A urinary sediment test is usually performed on a sample for which it has been determined that a urinary sediment test is necessary as a result of a urine qualitative test performed on the sample. However, there are also cases where a urinary sediment test is performed before a urine qualitative test and where only a urinary sediment test is performed. In the present embodiment, a plurality of sample containers respectively containing different samples are set in a rack, the rack is set in a sample analyzer, and testing of the samples are performed.

In the present embodiment, a urine analyzer 1 corresponds to the "sample analyzer" described in claims. A urine qualitative measurement part 10 corresponds to the "first measurement part" and the "qualitative measurement part" described in claims. A urinary sediment measurement part 20 corresponds to the "second measurement part" and the "sediment measurement part" described in claims. An information processing apparatus 40 corresponds to the "sample information processing apparatus" described in claims. A CPU 401 corresponds to the "controller" and the "output section" described in claims. A hard disk 404 corresponds to the "storage section" described in claims. A display section 420 corresponds to the "output section" and the "display section" described in claims. A service setting screen D1 corresponds to the "setting section" described in claims. Alarm symbols M1 and M2 correspond to the "information based on an excess of the time difference" described in claims. Elapsed time displaying regions M3 and M4 correspond to the "information based on an excess of the time difference" and the "time difference" described in claims. A set time period Ts corresponds to the "predetermined time period" described in claims. An elapsed time Tf corresponds to the "time difference" described in claims. An elapsed time Tc corresponds to the "time difference" described in claims. However, the above correspondence between the claims and the present embodiment is merely an example and does not limit the claims to the present embodiment.

Hereinafter, a urine analyzer according to the present embodiment will be described with reference to the drawings.

FIG. 1 shows an overall configuration of a system including a urine analyzer 1. The urine analyzer 1 according to the present embodiment includes a measurement unit 2, a transport unit 30, and an information processing apparatus 40.

The measurement unit 2 includes a urine qualitative measurement part 10 which performs urine qualitative tests and a urinary sediment measurement part 20 which performs urinary sediment tests. The urine qualitative measurement part 10 and the urinary sediment measurement part 20 are communicably connected to each other. Moreover, the urine qualitative measurement part 10 and the urinary sediment measurement part 20 are each communicably connected to the information processing apparatus 40. Further, the urine qualitative measurement part 10 is communicably connected to the transport unit 30.

The urine qualitative measurement part 10 is capable of measuring a sample for a plurality of measurement items (urine qualitative measurement items). The urine qualitative measurement items include glucose (GLU), protein (PRO), albumin (ALB), bilirubin (BIL), urobilinogen (URO), pH (PH), occult blood (BLD), ketone body (KET), nitrite (NIT), leukocyte (LEU), creatinine (CRE), and albumin/creatinine ratio (A/C).

The urinary sediment measurement part 20 is capable of measuring a sample for a plurality of measurement items (urinary sediment measurement items). The urinary sediment measurement items include red blood cell (RBC), white blood cell (WBC), epithelial cell (EC), cast (CAST), bacteria (BACT), crystal (X'TAL), yeast-like fungus (YLC), small round cell (SRC), and pathological cast (Path. CAST) including cell components, mucus thread (MUCUS), sperm (SPERM), urine conductivity (Cond.), red blood cell morphology information (RBC-Info.), urine concentration information (Cond.-Info.), and UTI (urinary tract infection) information (UTI-Info.).

The transport unit 30 is a single unit common for the urine qualitative measurement part 10 and the urinary sediment measurement part 20. The transport unit 30 is mounted to the front face of the measurement unit 2 and includes a transport path 31. The transport path 31 has a bottom face of a flat plate shape, provided at a lower level than the upper face of the transport unit 30. In a sample rack 50 which is transported on the transport path 31, ten holders are formed so as to be able to hold ten sample containers 51, respectively. By being held in a holder of the sample rack 50, each sample container 51 is transported on the transport path 31, along with the sample rack 50. A bar code label (not shown) for identifying a sample is affixed to a lateral side of the sample container 51. The information processing apparatus 40 is communicably connected to a host computer 60 via a communication line.

The transport path 31 is composed of a right vessel region 31a having a rectangular shape provided on the right side, a left vessel region 31c having a rectangular shape provided on the left side, and a connection region 31b which is connected to the right vessel region 31a and the left vessel region 31c. When a user places the sample rack 50 at the front side of the right vessel region 31a, this sample rack 50 is transported rearward (in the direction approaching the measurement unit 2), to be located at the rear end of the right vessel region 31a. Then, the sample rack 50 is transported leftward in the connection region 31b.

A bar code reader 106 reads out bar code information from the bar code label affixed to the sample container 51 located in front of the bar code reader 106. It should be noted that, the bar code reader 106 is controlled by a control section 101 of the urine qualitative measurement part 10 as described later.

The connection region 31b is provided with two aspirating positions for aspirating a sample from the sample container 51 held in the sample rack 50. From the sample container 51 located at one of the aspirating positions, the sample is aspirated by means of a nozzle (not shown) provided in the urine qualitative measurement part 10. From the sample container 51 located at the other of the aspirating positions, the sample is aspirated by means of a nozzle (not shown) provided in the urinary sediment measurement part 20. In this manner, aspiration of the sample contained in each sample container 51 on the connection region 31b is sequentially performed by the urine qualitative measurement part 10 and the urinary sediment measurement part 20.

When aspiration of all the samples held in the sample rack 50 has been completed, the sample rack 50 is transported leftward along the connection region 31b and located at the rear end of the left vessel region 31c. The sample rack 50 located at the rear of the left vessel region 31c is transported forward, to be sequentially located to the front side of the left vessel region 31c. Then, the sample rack 50 located at the front of the left vessel region 31c is taken out by the user.

Figure 2:
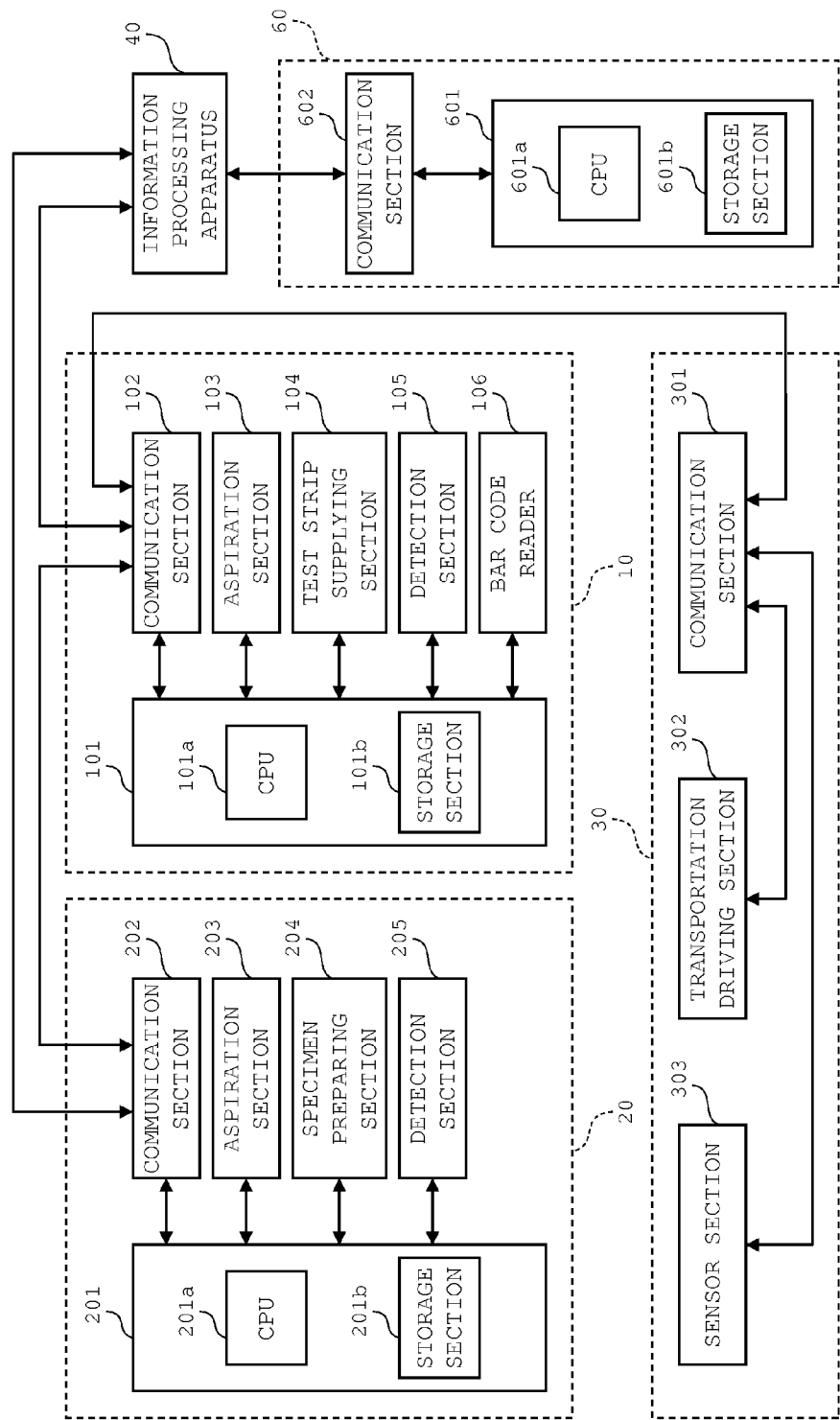
FIG. 2 shows configurations of a urine qualitative measurement part, a urinary sediment measurement part, a transport unit, and a host computer according to an embodiment.

FIG. 2 shows configurations of the urine qualitative measurement part 10, the urinary sediment measurement part 20, the transport unit 30, and the host computer 60.

The urine qualitative measurement part 10 includes the control section 101, a communication section 102, an aspiration section 103, a test strip supplying section 104, a detection section 105, and the bar code reader 106. The control section 101 includes a CPU 101a and a storage section 101b.

The CPU 101a executes computer programs stored in the storage section 101b and controls components of the urine qualitative measurement part 10. Further, the CPU 101a controls components of the transport unit 30 via the communication section 102. The storage section 101b includes storage means such as a ROM, a RAM, and a hard disk.

The communication section 102 processes signals from the control section 101 to output the resultant signals to the urinary sediment measurement part 20, the transport unit 30, and the information processing apparatus 40, and processes signals from the urinary sediment measurement part 20, the transport unit 30, and the information processing apparatus 40 to output the resultant signals to the control section 101. The aspiration section 103 aspirates, via a nozzle provided in the urine qualitative measurement part 10, the sample in the sample container 51 located at one of the aspirating positions described above. The test strip supplying section 104 takes out a test strip necessary for measurement from a test strip feeder in which test strips are stored, and applies as a spot the sample aspirated by the aspiration section 103 onto the taken-out test strip. The detection section 105 measures the test strip on which the sample has been applied as a spot. A measurement result obtained by the measurement is outputted to the control section 101 and analyzed by the CPU 101a. The bar code reader 106 reads out bar code information from the bar code label affixed to the sample container 51, and outputs the bar code information to the control section 101.

The urinary sediment measurement part 20 includes a control section 201, a communication section 202, an aspiration section 203, a specimen preparing section 204, and a detection section 205. The control section 201 includes a CPU 201a and a storage section 201b.

The CPU 201a executes computer programs stored in the storage section 201b and controls components of the urinary sediment measurement part 20. The storage section 201b includes storage means such as a ROM, a RAM, and a hard disk.

The communication section 202 processes signals from the control section 201 to output the resultant signals to the urine qualitative measurement part 10 and the information processing apparatus 40, and processes signals from the urine qualitative measurement part 10 and the information processing apparatus 40 to output the resultant signals to the control section 201. The aspiration section 203 aspirates, via the nozzle provided in the urinary sediment measurement part 20, the sample in the sample container 51 located at one of the supply positions described above. The specimen preparing section 204 mixes and stirs the sample aspirated by the aspiration section 203 and a reagent necessary for measurement, to prepare a specimen for measurement to be performed by the detection section 205. The detection section 205 measures the specimen prepared by the specimen preparing section 204, using a flow cytometer. A measurement result obtained by the measurement is outputted to the control section 201.

The transport unit 30 includes a communication section 301, a transportation driving section 302, and a sensor section 303. The communication section 301 processes signals from the urine qualitative measurement part 10 to output the resultant signals to components of the transport unit 30, and processes signals from components of the transport unit 30 to output the resultant signals to the urine qualitative measurement part 10. The transportation driving section 302 is controlled by the CPU 101a of the urine qualitative measurement part 10. The sensor section 303 includes various types of sensors provided in the transport unit 30, and outputs output signals from these sensors to the urine qualitative measurement part 10 via the communication section 301.

The host computer 60 includes a control section 601 and a communication section 602. The control section 601 includes a CPU 601a and a storage section 601b. The CPU 601a executes computer programs stored in the storage section 601b, and when receiving inquiries about a qualitative measurement order and a sediment measurement order from the information processing apparatus 40, the CPU 601a returns a qualitative measurement order and a sediment measurement order stored in the storage section 601b, respectively. The CPU 601a determines a sediment measurement order for the urinary sediment measurement part 20, based on a measurement result received from the urine qualitative measurement part 10 via the information processing apparatus 40 and criteria stored in the storage section 601b regarding whether measurement is necessary or not. The storage section 601b includes storage means such as a ROM, a RAM, and a hard disk.

Figure 3:
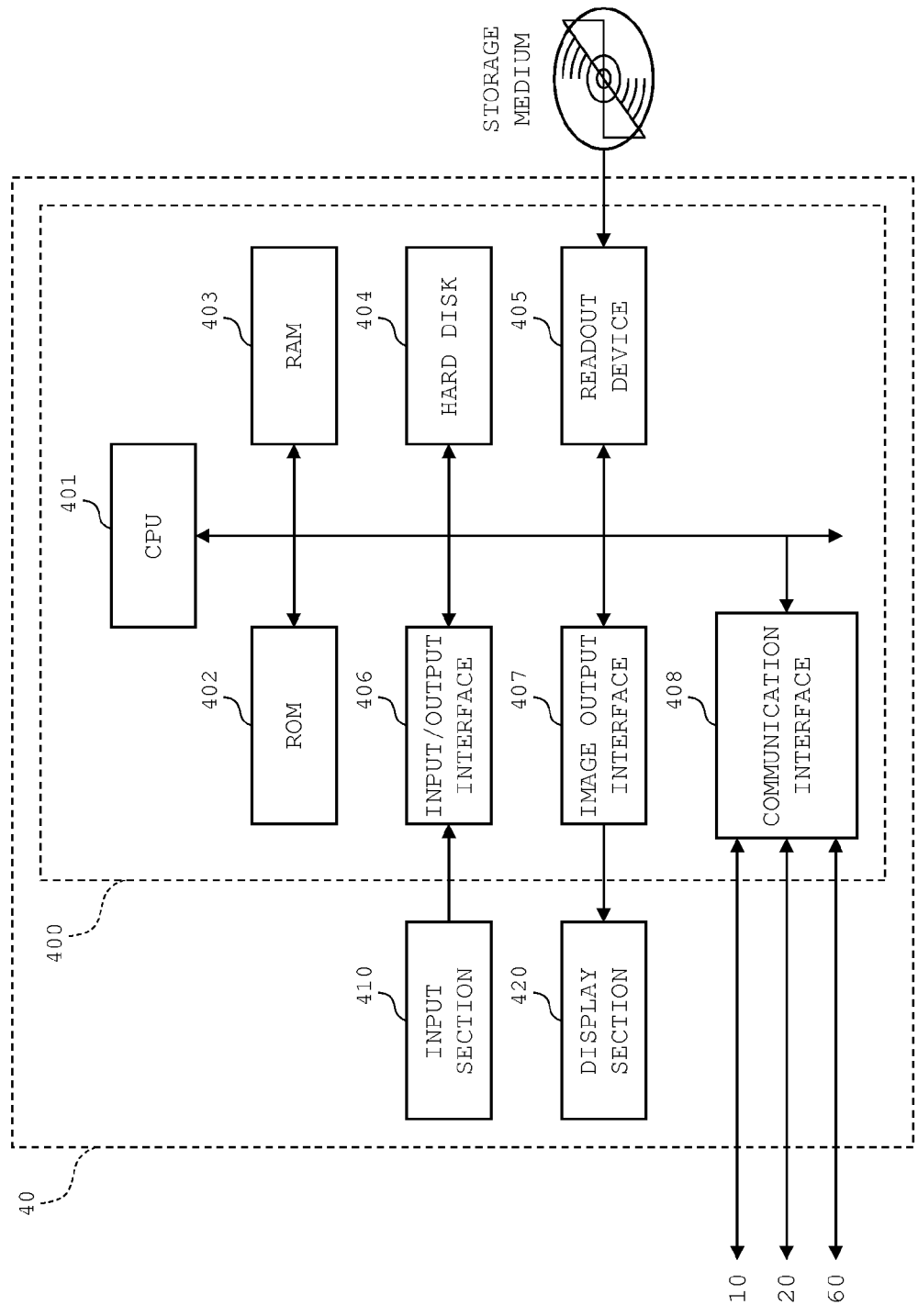
FIG. 3 shows a circuit configuration of an information processing apparatus according to an embodiment.

FIG. 3 shows a circuit configuration of the information processing apparatus 40.

The information processing apparatus 40 is implemented by a personal computer, and includes a body 400, an input section 410, and a display section 420. The body 400 includes a CPU 401, a ROM 402, a RAM 403, a hard disk 404, a readout device 405, an input/output interface 406, an image output interface 407, and a communication interface 408.

The CPU 401 executes computer programs stored in the ROM 402 and computer programs loaded onto the RAM 403. The CPU 401 inquires of the host computer 60 about a qualitative measurement order and a sediment measurement order, based on inquiries about a qualitative measurement order and a sediment measurement order received from the urine qualitative measurement part 10 and the urinary sediment measurement part 20. Further, the CPU 401 transmits the qualitative measurement order and the sediment measurement order received from the host computer 60 to the urine qualitative measurement part 10 and the urinary sediment measurement part 20, respectively.

The RAM 403 is used for reading out computer programs stored in the ROM 402 and the hard disk 404. The RAM 403 is also used as a work area for the CPU 401 when the CPU 401 executes these computer programs.

In the hard disk 404, various computer programs, such as an operating system and application programs, to be executed by the CPU 401, and data used for execution of such computer programs are stored. Moreover, in the hard disk 404, a program for displaying a service setting screen D1 (see FIG. 9B)), a result displaying screen D2 (see FIG. 10), and a merged data displaying screen D3 (see FIG. 11 to FIG. 15) is installed.

Moreover, in the hard disk 404, stored are: a qualitative measurement DB (database) (see FIG. 4A) in which results of qualitative measurements (qualitative measurement results) obtained by the urine qualitative measurement part 10 are stored; a sediment measurement DB (see FIG. 4B) in which results of sediment measurements (sediment measurement results) obtained by the urinary sediment measurement part 20 are stored; a merged DB (see FIG. 5A) based on the qualitative measurement results and the sediment measurement results; and a cross-check table (see FIG. 5B).

The readout device 405 is implemented by a CD drive, a DVD drive, or the like, and can read out computer programs and data stored in a storage medium. The input section 410 implemented by a mouse and a keyboard is connected to the input/output interface 406. By the user using the input section 410, data is inputted to the information processing apparatus 40. The image output interface 407 is connected to the display section 420 implemented by a display or the like, and outputs video signals corresponding to image data to the display section 420. The display section 420 displays an image based on the inputted video signals. Further, the communication interface 408 allows data transmission/reception with the urine qualitative measurement part 10, the urinary sediment measurement part 20, and the host computer 60.

FIG. 4A illustrates a concept of a configuration of the qualitative measurement DB.

As shown in FIG. 4A, the qualitative measurement DB includes a number item, a sample number item, a measurement date item, a measurement time item, and a measurement result item for storing a plurality of results of a qualitative measurement. In the number item, a number for uniquely identifying a record (line) is stored. In the sample number item, a sample number assigned to each sample is stored. In the measurement date item and the measurement time item, the date and time at which the measurement by the urine qualitative measurement part 10 was performed are stored. In the measurement result item, a plurality of results of a qualitative measurement performed by the urine qualitative measurement part 10 are stored.

It is sufficient that the qualitative measurement time stored in the qualitative measurement DB is a time relevant to the qualitative measurement. Thus, the time at which the sample was aspirated, the time at which measurement operations on the sample ended, the time at which the measurement result was obtained by analyzing data, or the like is used.

It should be noted that each item in the qualitative measurement DB is stored with some past history thereof retained. That is, the qualitative measurement DB includes a plurality of lines, and information fit within the plurality of lines is not deleted even if new information is inputted.

FIG. 4B illustrates a concept of a configuration of the sediment measurement DB.

As shown in FIG. 4B, the sediment measurement DB includes a number item, a sample number item, a measurement date item, a measurement time item, a measurement result item for storing a plurality of results of a sediment measurement. In the number item, a number for uniquely identifying a record (line) is stored. In the sample number item, a sample number assigned to each sample is stored. In the measurement date item and the measurement time item, the date and time at which the measurement by the urinary sediment measurement part 20 was performed are stored. In the measurement result item, a plurality of results of a sediment measurement performed by the urinary sediment measurement part 20 are stored.

It is sufficient that the sediment measurement time stored in the sediment measurement DB is a time relevant to the sediment measurement. Thus, the time at which the sample was aspirated, the time at which measurement operations on the sample ended, the time at which the measurement result was obtained by analyzing data, or the like is used.

It should be noted that each item in the sediment measurement DB is stored with some past history thereof retained. That is, the sediment measurement DB includes a plurality of lines, and information fit within the plurality of lines is not deleted even if new information is inputted.

FIG. 5A illustrates a concept of a configuration of a merged DB.

As shown in FIG. 5A, the merged DB includes a number item, a measurement date item, a measurement time item, a qualitative number item, a sediment number item, a cross-check result item, a measurement elapsed time item, and a reliability item. In the number item, a number for uniquely identifying a record (line) is stored. In the measurement date item and the measurement time item, the date and time at which the record was generated in the merged DB are stored. In the qualitative number item and the sediment number item, the number in the number item of the qualitative measurement DB and the number in the number item of the sediment measurement DB are stored, respectively. It should be noted that, in the case where there is no corresponding number item in the qualitative measurement DB or no corresponding number item in the sediment measurement DB, 0 is stored in the qualitative number item or the sediment number item.

It should be noted that each item in the merged DB is stored with some past history thereof retained. That is, the merged DB includes a plurality of lines, and information fit within the plurality of lines is not deleted even if new information is inputted.

In the cross-check result item, a result of a cross-check is stored as appropriate, the cross-check being performed based on a qualitative measurement result obtained from the qualitative measurement DB by using the number in the qualitative number item, and a sediment measurement result obtained from the sediment measurement DB by using the number in the sediment number item. As a result of a cross-check, with respect to any check target (check item) in the cross-check table shown in FIG. 5B, if there is an incompatible relationship (error) between the qualitative measurement result and the sediment measurement result, the number in the number item of the cross-check table corresponding to that check item is stored in the cross-check result item. In the cross-check result item, each record (line) is provided with ten columns for each entering the number, in the number item of the cross-check table, for which an error has been determined. In a column in which no number in the number item of the cross-check table is entered, 0 is stored.

In the measurement elapsed time item, an elapsed time Tf (minute: second) from the qualitative measurement time to the sediment measurement time, or an elapsed time Tc (minute: second) from the sediment measurement time to the qualitative measurement time is stored. That is, in a case where the sediment measurement time was later than the qualitative measurement time, an elapsed time Tf is stored in the measurement elapsed time item. In a case where the qualitative measurement time was later than the sediment measurement time, an elapsed time Tc is stored in the measurement elapsed time item. It should be noted that when there is no corresponding number item in the qualitative measurement DB or there is no corresponding number item in the sediment measurement DB, 0 is stored in the measurement elapsed time item.

In the reliability item, a result of a reliability evaluation is stored which is performed based on the measurement elapsed time Tf or Tc and a predetermined set time period Ts stored in advance. It should be noted that the set time period Ts can be set by the user. The method for setting the set time period Ts will be described later with reference to FIGS. 9A and 9B.

In a case where the elapsed time Tf from the qualitative measurement time to the sediment measurement time or the elapsed time Tc from the sediment measurement time to the qualitative measurement time exceeds the predetermined set time period Ts, it is determined that the reliability of the measurement is low since the sample has deteriorated. Thus, in the reliability item, 1 is stored as a low reliability flag. In a case where the elapsed time Tf from the qualitative measurement time to the sediment measurement time or the elapsed time Tc from the sediment measurement time to the qualitative measurement time does not exceed the predetermined set time period Ts, it is determined that the reliability of the measurement is high. Thus, in the reliability item, 0 is stored as a high reliability flag. It should be noted that when there is no corresponding number item in the qualitative measurement DB or there is no corresponding number item in the sediment measurement DB, 0 is stored in the reliability item.

FIG. 5B illustrates a concept of a configuration of the cross-check table.

As shown in FIG. 5B, the cross-check table includes a number item, a target item, and a detail item. In the number item, a number for uniquely identifying a record (line) is stored. In the target item, a combination of a measurement item for the urine qualitative measurement part 10 and a measurement item for the urinary sediment measurement part 20, that is, a qualitative measurement item and a sediment measurement item (check item) targeted by the cross-check, is stored. In the detail item, information is stored that is used for determining whether a measurement result regarding a qualitative measurement item and a measurement result regarding a sediment measurement item targeted by a cross-check are in a predetermined relationship.

For example, in the detail item of number 3 of the cross-check table, information used for setting a determination criterion shown in FIG. 5C is stored. In FIG. 5C, the horizontal axis represents the level of measurement values of "CAST" in qualitative measurement results, and the vertical axis represents the level of measurement values of "PRO" in sediment measurement results. In this case, when the intersection of the level of a "CAST" measurement value and the level of a "PRO" measurement value is included in the white area (normal), it is determined that the level of the "CAST" measurement value and the level of the "PRO" measurement value are in a compatible relationship (normal), and when the intersection thereof is included in the black area (error), it is determined that the level of the "CAST" measurement value and the level of the "PRO" measurement value are in an incompatible relationship (error). Determinations regarding other check items listed in the cross-check table are performed in the same manner.

When performing a cross-check, with respect to a qualitative measurement result and a sediment measurement result, their values corresponding to the two measurement items shown in each target item in the cross-check table are compared with the determination criterion shown in the corresponding detail item, and it is determined whether or not they are in an incompatible relationship. If they are in an incompatible relationship, the number in the number item of the cross-check table corresponding to that check item is stored in the cross-check result item in the merged DB.

FIG. 6 is a flow chart showing a merging process performed by the information processing apparatus 40 during qualitative measurement processing.

Based on an inquiry about a qualitative measurement order received from the urine qualitative measurement part 10, the CPU 401 of the information processing apparatus 40 transmits an inquiry about the qualitative measurement order to the host computer 60, and then, the CPU 401 causes the processing to wait until receiving an inquiry result (qualitative measurement order) from the host computer 60 (S101). Upon receiving a qualitative measurement order (S101: YES), the CPU 401 transmits the received qualitative measurement order to the urine qualitative measurement part 10, and determines, based on information of whether measurement is necessary included in this qualitative measurement order, whether a measurement by the urine qualitative measurement part 10 is necessary (S102).

When a measurement by the urine qualitative measurement part 10 is necessary (S102: YES), the CPU 401 generates a new record in the qualitative measurement DB (S103). In this new record, a number unique to the record is stored in the number item, the sample number included in the qualitative measurement order is stored in the sample number item, and the other items than these two items remain blank.

Subsequently, the CPU 401 causes the processing to wait until receiving a qualitative measurement result from the urine qualitative measurement part 10 after the measurement by the urine qualitative measurement part 10 has ended (S104). Upon receiving the qualitative measurement result (S104: YES), the CPU 401 stores the received qualitative measurement result in the qualitative measurement DB (S105). That is, in the measurement date and the measurement time of the record generated in S103, the measurement date and time included in the received qualitative measurement result are stored, respectively. Further, in the measurement result item of the record generated in S103, corresponding measurement results included in the received qualitative measurement result are stored.

Subsequently, the CPU 401 determines whether one or more measurement results having the same sample number as the sample number included in the received qualitative measurement result have been stored in the sediment measurement DB (S106). When one or more measurement results having the same sample number have been stored in the sediment measurement DB (S106: YES), the CPU 401 determines whether one or more sediment measurement results within the set time period Ts before the current time have been stored in the sediment measurement DB (S107). That is, it is determined whether their elapsed time Tc from the sediment measurement time to the qualitative measurement time is within the set time period Ts. When no measurement result having the same sample number has been stored in the sediment measurement DB (S106: NO), the processing is advanced to S114. When one or more sediment measurement results within the set time period Ts before the current time have been stored in the sediment measurement DB (S107: YES), the processing is advanced to S108. When no such measurement result has been stored in the sediment measurement DB (S107: NO), the processing is advanced to S110.

When it has been determined as YES in S107, the CPU 401 performs a cross-check using the received qualitative measurement result and the latest sediment measurement result among one or more such sediment measurement results (S108). For determination performed in the cross-check, the cross-check table shown in FIG. 5B is used.

Subsequently, the CPU 401 stores a link to the qualitative measurement result, a link to the latest sediment measurement result, a cross-check result obtained in S108, an elapsed time Tc from the latest sediment measurement to the qualitative measurement, and the high reliability flag, in the merged DB (S109). That is, the CPU 401 generates a new record in the merged DB and stores the date and time at which this new record was generated, in the measurement date and the measurement time of this record. Further, in the qualitative number item and the sediment number item of this record, the number in the number item of the qualitative measurement DB representing the qualitative measurement result used in the cross-check, and the number in the number item of the sediment measurement DB representing the sediment measurement result used in the cross-check are stored, respectively. Further, in the cross-check result item of this record, results of the cross-check are stored as appropriate.

Further, in the measurement elapsed time item of this record, an elapsed time (i.e., elapsed time Tc) is stored which is obtained by calculating the difference between the measurement time in the sediment measurement DB corresponding to the latest sediment measurement result and the measurement time in the qualitative measurement DB corresponding to this qualitative measurement result. Further, in the reliability item of this record, since the qualitative measurement was performed within the set time period Ts, 0 is stored as the high reliability flag indicating that the reliability of the measurement is high.

When it has been determined as NO in S107, the CPU 401 stores a link to the received qualitative measurement result, a link to the latest sediment measurement result, an elapsed time Tc from the latest sediment measurement to the qualitative measurement, and the low reliability flag, in the merged DB (S110). That is, the CPU 401 generates a new record in the merged DB and stores the date and time at which this new record was generated, in the measurement date and the measurement time of this record. Further, in the qualitative number item of this record, the number in the number item of the qualitative measurement DB representing the received qualitative measurement result is stored. Further, in the sediment number item of this record, the number in the number item of the sediment measurement DB representing the latest sediment measurement result among the one or more sediment measurement results obtained before the set time period Ts is stored. Further, in the measurement elapsed time item of this record, an elapsed time (i.e., elapsed time Tc) is stored which is obtained by calculating the difference between the measurement time in the sediment measurement DB corresponding to the latest sediment measurement result and the measurement time in the qualitative measurement DB corresponding to the received qualitative measurement result. Further, in the reliability item of this record, since the sediment measurement was not performed within the set time period Ts, 1 is stored as the low reliability flag indicating that the reliability of the sample is low.

Next, when a measurement by the urine qualitative measurement part 10 is not necessary (S102: NO), the CPU 401 determines whether one or more measurement results having the same sample number as the sample number included in the received qualitative measurement result have been stored in the sediment measurement DB (S111). When one or more measurement results having the same sample number have been stored in the sediment measurement DB (S111: YES), the CPU 401 determines whether one or more sediment measurement results within the set time period Ts before the current time have been stored in the sediment measurement DB (S112). When no measurement result having the same sample number has been stored in the sediment measurement DB (S111: NO), the processing is advanced to S114. Also, when it has been determined as NO in S112, the processing is advanced to S114.

When it has been determined as YES in S112, the CPU 401 stores a link to the latest sediment measurement result among one or more such sediment measurement results, in the merged DB (S113). That is, the CPU 401 generates a new record in the merged DB and stores the date and time at which this new record was generated, in the measurement date and the measurement time of this record. Further, in the sediment number item of this record, the number in the number item of the sediment measurement DB representing the latest sediment measurement result among the one or more sediment measurement results of the same sample and within the set time period Ts is stored. Further, 0 is stored in the qualitative number item, the cross-check result item, the measurement elapsed time item, and the reliability item of this record.

When the user has not performed a shutdown process for the information processing apparatus 40 (S114: NO), the CPU 401 repeats the processes of S101 to S113, and when the user has performed the shutdown process (S114: YES), the CPU 401 ends the processing.

FIG. 7 is a flow chart showing a merging process performed by the information processing apparatus 40 during sediment measurement processing.

Based on an inquiry about a sediment measurement order received from the urinary sediment measurement part 20, the CPU 401 of the information processing apparatus 40 transmits an inquiry about the sediment measurement order to the host computer 60, and then, the CPU 401 causes the processing to wait until receiving an inquiry result (sediment measurement order) from the host computer 60 (S201). Upon receiving a sediment measurement order (S201: YES), the CPU 401 transmits the received sediment measurement order to the urinary sediment measurement part 20, and determines, based on information of whether measurement is necessary included in this sediment measurement order, whether a measurement by the urinary sediment measurement part 20 is necessary (S202).

When a measurement by the urinary sediment measurement part 20 is necessary (S202: YES), the CPU 401 generates a new record in the sediment measurement DB (S203). In this new record, a number unique to the record is stored in the number item, the sample number included in the sediment measurement order is stored in the sample number item, and the other items than these two items remain blank.

Subsequently, the CPU 401 causes the processing to wait until receiving a sediment measurement result from the urinary sediment measurement part 20 after the measurement by the urinary sediment measurement part 20 has ended (S204). Upon receiving the sediment measurement result (S204: YES), the CPU 401 stores the received sediment measurement result in the sediment measurement DB (S205). That is, in the measurement date and the measurement time of the record generated in S203, the measurement date and time included in the received sediment measurement result are stored, respectively. Further, in the measurement result item of the record generated in S203, corresponding measurement results included in the received sediment measurement result are stored.

Subsequently, the CPU 401 determines whether one or more measurement results having the same sample number as the sample number included in the received sediment measurement result have been stored in the qualitative measurement DB (S206). When one or more measurement results having the same sample number have been stored in the qualitative measurement DB (S206: YES), the CPU 401 determines whether one or more qualitative measurement results within the set time period Ts before the current time have been stored in the qualitative measurement DB (S207). That is, it is determined whether their elapsed time Tf from the qualitative measurement time to the sediment measurement time is within the set time period Ts. When no measurement result having the same sample number has been stored in the qualitative measurement DB (S206: NO), the processing is advanced to S214. When one or more qualitative measurement results within the set time period Ts before the current time have been stored in the qualitative measurement DB (S207: YES), the processing is advanced to S208. When no such qualitative measurement result has been stored in the qualitative measurement DB (S207: NO), the processing is advanced to S210.

When it has been determined as YES in S207, the CPU 401 performs a cross-check using the latest qualitative measurement result among one or more such qualitative measurement results and the received sediment measurement result (S208). For determination performed in the cross-check, the cross-check table shown in FIG. 5B is used.

Subsequently, the CPU 401 stores a link to the latest qualitative measurement result, a link to this sediment measurement result, and a cross-check result obtained in S208, an elapsed time Tf from the latest qualitative measurement to the sediment measurement, and a high reliability flag, in the merged DB (S209). That is, the CPU 401 generates a new record in the merged DB and stores the date and time at which this new record was generated, in the measurement date and the measurement time of this record. Further, in the qualitative number item and the sediment number item of this record, the number in the number item of the qualitative measurement DB representing the qualitative measurement result used in the cross-check, and the number in the number item of the sediment measurement DB representing the sediment measurement result used in the cross-check are stored, respectively. Further, in the cross-check result item of this record, results of the cross-check are stored as appropriate.

Further, in the measurement elapsed time item of this record, an elapsed time (i.e., elapsed time Tf) is stored which is obtained by calculating the difference between the measurement time in the qualitative measurement DB corresponding to the latest qualitative measurement result and the measurement time in the sediment measurement DB corresponding to this sediment measurement result. Further, in the reliability item of this record, since the sediment measurement was performed within the set time period Ts, 0 is stored as the high reliability flag indicating that the reliability of the measurement is high.

When it has been determined as NO in S207, the CPU 401 stores a link to the latest qualitative measurement result, a link to the received sediment measurement result, an elapsed time Tf from the latest qualitative measurement to the sediment measurement, and the low reliability flag, in the merged DB (S210). That is, the CPU 401 generates a new record in the merged DB and stores the date and time at which this new record was generated, in the measurement date and the measurement time of this record. Further, in the sediment number item of this record, the number in the number item of the sediment measurement DB representing the received sediment measurement result is stored. Further, in the qualitative number item of this record, the number in the number item of the qualitative measurement DB representing the latest qualitative measurement result among the one or more qualitative measurement results obtained before the set time period Ts is stored. Further, in the measurement elapsed time item of this record, an elapsed time (i.e., elapsed time Tf) is stored which is obtained by calculating the difference between the measurement time in the qualitative measurement DB representing the latest qualitative measurement result and the time at which this new record was generated. Further, in the reliability item of this record, since the qualitative measurement was not performed within the set time period Ts, 1 is stored as the low reliability flag representing that the reliability of the sample is low.

Next, when a measurement by the urinary sediment measurement part 20 is not necessary (S202: NO), the CPU 401 determines whether one or more measurement results having the same sample number as the sample number included in the received sediment measurement result have been stored in the qualitative measurement DB (S211). When one or more measurement results having the same sample number have been stored in the qualitative measurement DB (S211: YES), the CPU 401 determines whether one or more qualitative measurement results within the set time period Ts before the current time have been stored in the qualitative measurement DB (S212). When no measurement result having the same sample number has been stored in the qualitative measurement DB (S211: NO), the processing is advanced to S214. Also, when it has been determined as NO in S212, the processing is advanced to S214.

When it has been determined as YES in S212, the CPU 401 stores a link to the latest qualitative measurement result among one or more such qualitative measurement results, in the merged DB (S213). That is, the CPU 401 generates a new record in the merged DB, and stores the date and time at which this new record was generated, in the measurement date and the measurement time of this record. Further, in the qualitative number item of this record, the number in the number item of the qualitative measurement DB representing the latest qualitative measurement result among the one or more qualitative measurement results of the same sample and within the set time period Ts is stored. Further, 0 is stored in the sediment number item, the cross-check result item, the measurement elapsed time item, and the reliability item of this record.

When the user has not performed a shutdown process for the information processing apparatus 40 (S214: NO), the CPU 401 repeats the processes of S201 to S213, and when the user has performed the shutdown process (S214: YES), the CPU 401 ends the processing.

Figure 8B:
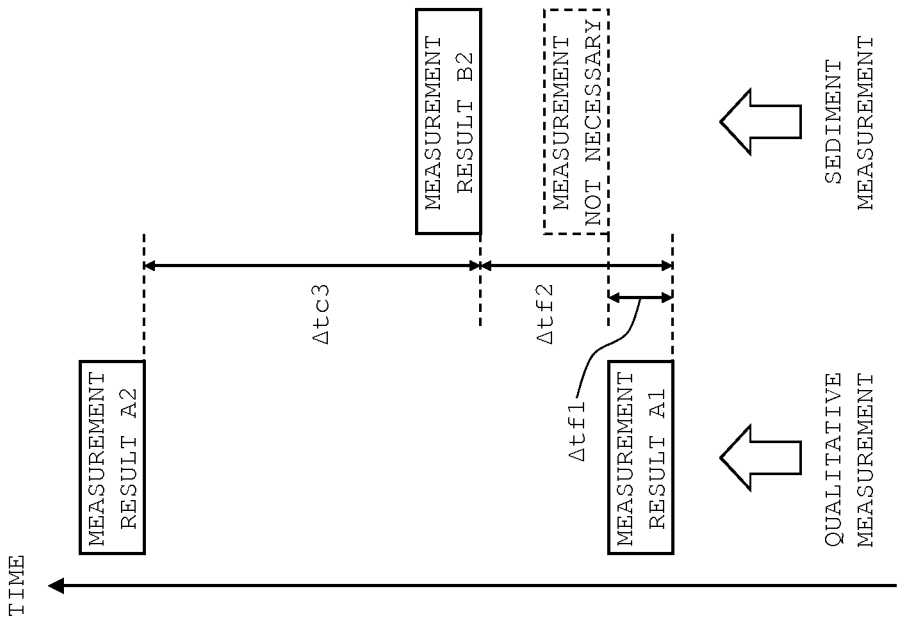
FIGS. 8A and 8B illustrate examples of a merging process according to an embodiment.
Figure 8A:
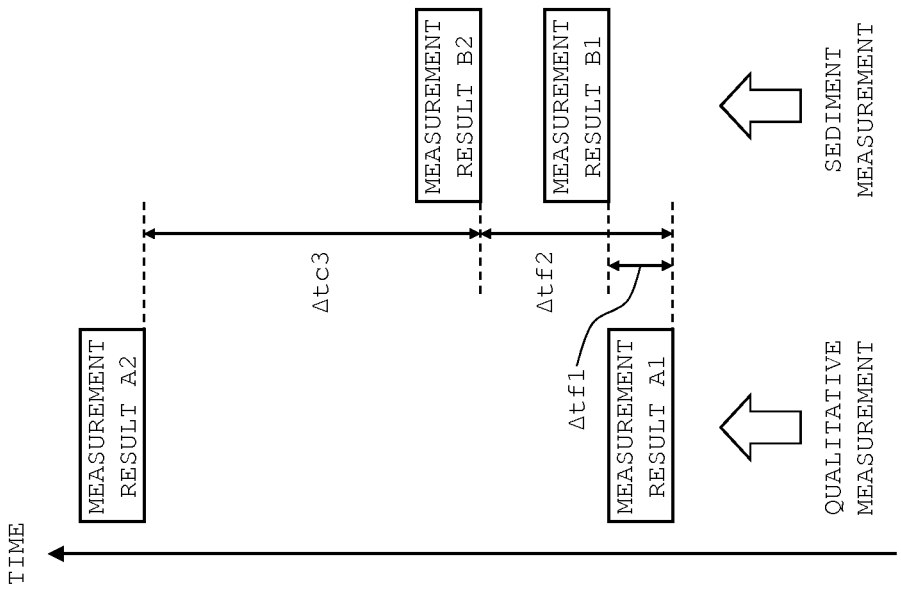

FIG. 8A illustrates an example of the merging process.

In FIG. 8A, the vertical axis represents time. FIG. 8A shows that the information processing apparatus 40 received qualitative measurement results A1 and A2 and sediment measurement results B1 and B2, along the time axis. It should be noted that these measurements were all performed onto the same sample, and the dates and times at which the respective measurements were performed and the dates and times at which the information processing apparatus 40 received these measurement results are the same, respectively. It is assumed that: the time difference between the time at which the measurement result A1 was obtained and the time at which the measurement result B1 was obtained is $\Delta tf1$; the time difference between the time at which the measurement result A1 was obtained and the time at which the measurement result B2 was obtained is $\Delta tf2$; and the time difference between the time at which the measurement result B2 was obtained and the time at which the measurement result A2 was obtained is $\Delta tc3$. Moreover, it is assumed that $\Delta tf1$ and $\Delta tf2$ are each shorter than the set time period Ts mentioned above, and $\Delta tc3$ is longer than the set time period Ts.

The measurement result A1 and the measurement result B1 were obtained when a sample container 51 containing the sample and held in a sample rack 50 was transported by the transport unit 30 along the transport path 31 for the first time. The measurement result B2 was obtained when the sample container 51 containing the sample and held in the sample rack 50 was transported by the transport unit 30 along the transport path 31 for the second time. In this case, an order to perform only a urinary sediment measurement on the sample is registered in the host computer 60. The measurement result A2 was obtained when the sample container 51 containing the sample and held in the sample rack 50 was transported by the transport unit 30 along the transport path 31 for the third time. In this case, an order to perform only a urine qualitative measurement on the sample is registered in the host computer 60.

With reference to FIG. 8A, as a result of making an inquiry about a qualitative measurement order with the host computer 60, if it has been determined that a qualitative measurement is necessary, a qualitative measurement is performed on the sample, and the measurement result A1 is obtained. At the time when the measurement result A1 was obtained, since no sediment measurement on the same sample had been performed, no cross-check is performed, and no record is added to the merged DB based on the measurement result A1.

Subsequently, with respect to this sample, an inquiry about a sediment measurement order is made with the host computer 60. When the host computer 60 has determined, based on the measurement result A1, that a sediment measurement is necessary, the host computer 60 transmits an order to perform a sediment measurement on this sample, to the information processing apparatus 40. Accordingly, the sediment measurement is performed and the measurement result B1 is obtained. At the time when the measurement result B1 was obtained, since the measurement result A1 had been obtained by $\Delta tf1$ ($\Delta tf1<Ts$) therebefore, a cross-check is performed based on the measurement results A1 and B1, and a record is added to the merged DB. In this record, results of the cross-check, $\Delta tf1$, and the high reliability flag 0 are respectively included in the cross-check result item, the measurement elapsed time item, and the reliability item.

Subsequently, in order to perform only a sediment measurement again, the user sets, in the host computer 60, a qualitative measurement order and a sediment measurement order such that only a sediment measurement is performed on this sample. Then, the user sets this sample in the right vessel region 31a again, and starts the measurement. Thereafter, as a result of making an inquiry about a qualitative measurement order and a sediment measurement order with the host computer 60, no qualitative measurement is performed on this sample, and only a sediment measurement is performed on this sample, whereby the measurement result B2 is obtained. At the time when the measurement result B2 was obtained, since the measurement result A1 had been obtained by $\Delta tf2$ ($\Delta tf2<Ts$) therebefore, a cross-check is performed based on the measurement results A1 and B2, and a record is added to the merged DB. In this record, results of the cross-check, $\Delta tf2$, and the high reliability flag 0 are respectively included in the cross-check result item, the measurement elapsed time item, and the reliability item.

As a result, the record based on the measurement results A1 and B1 and the record based on the measurement results A1 and B2 are both stored in the merged DB.

Subsequently, in order to perform only a qualitative measurement again, the user sets a qualitative measurement order and a sediment measurement order in the host computer 60. As a result of making an inquiry about a qualitative measurement order with the host computer 60, a qualitative measurement is performed on this sample, and the measurement result A2 is obtained. Then, an inquiry about a sediment measurement order is made with the host computer 60, and a response is made to the effect that no sediment measurement is performed on this sample. Accordingly, a sediment measurement is skipped. At the time when the measurement result A2 was obtained, since the measurement result B2 had been obtained by $\Delta tc3$ therebefore, which is longer than the set time period Ts described above, no cross-check is performed based on the measurement results A2 and B2. Then, a record is added to the merged DB, along with information indicating a low reliability. That is, in the record in the merged DB, $\Delta tc3$, which is longer than the set time period Ts described above, is stored in the measurement elapsed time item, and 1 is stored in the reliability item as the low reliability flag.

As a result, three records, that is, the record based on the measurement results A1 and B1, the record based on the measurement results A1 and B2, and the record based on the measurement results A2 and B2, are stored in the merged DB.

FIG. 8B illustrates a case where, as a result of making an inquiry about a sediment measurement order with the host computer 60 at the timing when the measurement result B1 is obtained as shown in FIG. 8A, it has been determined that a sediment measurement is not necessary.

In this case, at the time when it has been determined that a sediment measurement is not necessary, since the measurement result A1 had been obtained by $\Delta tf1$ therebefore, a record is added to the merged DB based only on the measurement result A1. At this time, as shown in FIG. 5A, in the record added to the merged DB, 0 is stored in the sediment number item and all the columns of the cross-check result item.

FIG. 9A is a flow chart showing a setting process performed by the information processing apparatus 40.

The CPU 401 of the information processing apparatus 40 determines whether the user has made an instruction to display the service setting screen D1 via the input section 410

(S301). When an instruction to display the service setting screen D1 has been made (S301: YES), the CPU 401 reads, from the hard disk 404, contents of settings of setting items described below, and displays the service setting screen D1 on the display section 420 (S302).

FIG. 9B shows the service setting screen D1. The service setting screen D1 includes a setting item displaying region D11, an input region D12, an OK button D13, and a cancel button D14.

In the setting item displaying region D11, a plurality of changeable setting items regarding the information processing apparatus 40 are displayed. The setting items displayed in the setting item displaying region D11 include the set time period Ts used in S107 in FIG. 6 and S207 in FIG. 7. When the user clicks a setting item in the setting item displaying region D11, the clicked item is displayed in a reversed manner as shown in FIG. 9B, and the content of the setting of this setting item is displayed in the input region D12. The setting item displayed in the reversed manner in FIG. 9B is an item regarding the set time period Ts used in S107 in FIG. 6 and S207 in FIG. 7. The user can change the content of the setting item by rewriting the content displayed in the input region D12 and clicking the OK button D13.

Here, the default value (the value in the initial state) of the set time period Ts in the present embodiment is set to be 30 (minutes). The default value of the set time period Ts is preferably set to be a value that allows a cross-check to be performed even when a reagent or a test strip is replaced between a measurement performed by the urine qualitative measurement part 10 and a measurement performed by the urinary sediment measurement part 20. That is, the default value is preferably set to be longer than or equal to a time period (e.g., 15 minutes) that is assumed to be necessary for a reagent or a test strip to be replaced. Moreover, the default value of the set time period Ts is preferably set to be a value that can maintain the accuracy of a measurement result. A result of a measurement of a sample deteriorated due to lapse of time is considered to have a low accuracy, and thus, in order to prevent a cross-check from being performed based on such a measurement result, the default value of the set time period Ts is preferably set to be shorter than or equal to a time period (e.g., 60 minutes) that is considered to be able to maintain the accuracy of a measurement result.

It should be noted that, when the set time period Ts is set to be 0, it is always determined as NO in S107 in FIG. 6 and S207 and FIG. 7, and thus, a cross-check is prevented from being performed.

With reference back to FIG. 9A, when the service setting screen D1 is displayed (S302), the CPU 401 of the information processing apparatus 40 causes the processing to wait until the OK button D13 or the cancel button D14 is clicked. When the OK button D13 has been clicked (S303: YES), the CPU 401 stores the content of the setting rewritten by the user in the hard disk 404 (S304). When the cancel button D14 has been clicked, (S303: NO, S305: YES), the processing is advanced to S306.

When the user has not performed a shutdown process for the information processing apparatus 40 (S306: NO), the CPU 401 repeats the processes of S301 to S305, and when the user has performed the shutdown process (S306: YES), the processing ends.

Figure 10:
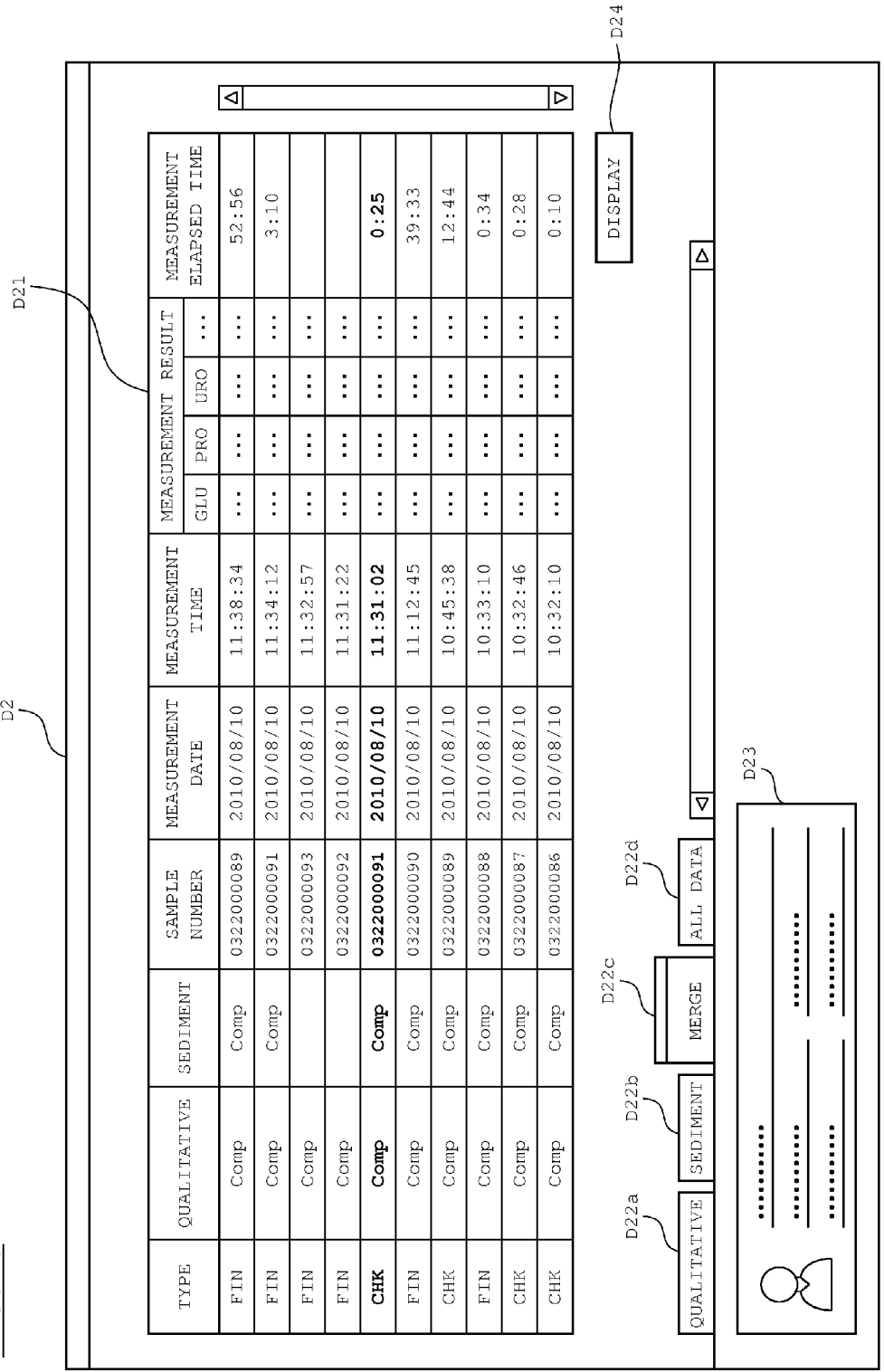
FIG. 10 shows a result displaying screen for displaying results of a measurement performed by a urine analyzer according to an embodiment.

FIG. 10 shows the result displaying screen D2 for displaying results of measurements performed by the urine analyzer 1. The result displaying screen D2 is displayed on the display section 420, in accordance with an instruction to display it made by the user.

The result displaying screen D2 includes a list displaying region D21, switching tabs D22a to D22d, a patient information displaying region D23, and a display button D24.

The list displaying region D21 is configured such that its display is switched in accordance with a switching tab selected from among the switching tabs D22a to D22d. FIG. 10 shows a state where merged data based on the merged DB is displayed with the switching tab D22c selected. In the list displaying region D21 in this state, a type item, a qualitative item, a sediment item, a sample number item, a measurement date item, a measurement time item, a measurement result item for storing a plurality of results of the measurements, and a measurement elapsed time item are displayed.

In the type item, a character string of "FIN" or "CHK" is displayed. When "FIN" is displayed, it indicates that the merged data shown in this line includes no check item determined as an error (all 0s) in the cross-check result item. When "CHK" is displayed, it indicates that the merged data shown in this line includes a check item determined as an error in the cross-check result item.

In the qualitative item and the sediment item, information regarding the measurement performed by the urine qualitative measurement part 10 and information regarding the measurement performed by the urinary sediment measurement part are displayed, respectively. When "Comp" is displayed in these items, it indicates that measurement results shown in the merged data of this line were normally obtained.

In the sample number item, the sample number based on which the merged data shown in this line was generated is displayed. In the measurement date item and the measurement time item, the measurement date item and measurement time item of the merged DB are displayed, respectively. The measurement result item includes all the qualitative measurement items and all the sediment measurement items, and results of the corresponding qualitative measurement and results of the corresponding sediment measurement are displayed. In the measurement elapsed time item, the elapsed time Tf from the qualitative measurement result to the sediment measurement, or the elapsed time Tc from the sediment measurement result to the qualitative measurement is displayed. That is, in the measurement elapsed time item, the information stored in the measurement elapsed time item of the merged DB is displayed. It should be noted that, when only the qualitative measurement or the sediment measurement was performed, the measurement elapsed time item remains blank.

When one of the switching tabs D22a to D22c is clicked, corresponding qualitative measurement results based on the qualitative measurement DB, sediment measurement results based on the sediment measurement DB, or merged data based on the merged DB are displayed in the list displaying region D21. When the switching tab D22d is clicked, all of the information displayed when each of the switching tabs D22a to D22c is clicked is displayed in the list displaying region D21.

In the patient information displaying region D23, patient information obtained based on the sample number of the line clicked in the list displaying region D21 is displayed. When a line in the list displaying region D21 is clicked while merged data is shown in the list displaying region D21 as shown in FIG. 10, and then the display button D24 is clicked while the line is displayed in the reversed manner as shown in FIG. 10, the detail of the merged data shown in this line is displayed in the merged data displaying screen D3.

Figure 11:
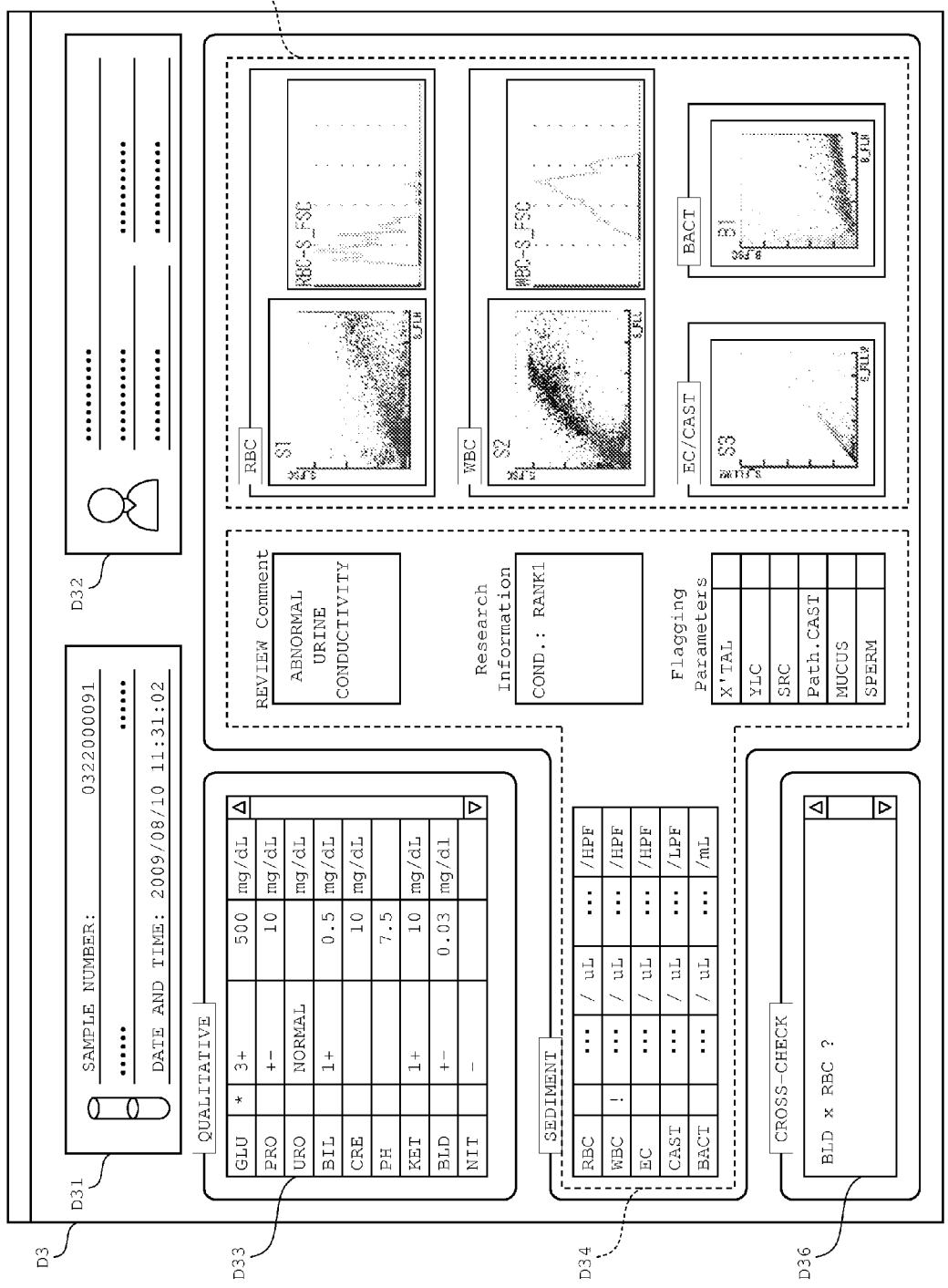
FIG. 11 shows a merged data displaying screen according to an embodiment.

FIG. 11 shows the merged data displaying screen D3. In the merged data displaying screen D3 shown in FIG. 11, the merged data of the fifth line from the top of the list displaying region D21 shown in FIG. 10 is displayed.

The merged data displaying screen D3 includes a sample information displaying region D31, a patient information displaying region D32, a qualitative measurement result displaying region D33, sediment measurement result displaying regions D34 and D35, and a cross-check result displaying region D36.

In the sample information displaying region D31, information of the sample which is the source of the measurement results displayed in the merged data displaying screen D3 is displayed. In the patient information displaying region D32, information of the patient from whom the sample was collected is displayed.

In the qualitative measurement result displaying region D33, a list of results of the qualitative measurement is displayed. In the sediment measurement result displaying region D34, a list of results of the sediment measurement is displayed. In the sediment measurement result displaying region D35, the results of the sediment measurement are displayed in scattergrams. In the cross-check result displaying region D36, results of the cross-checks performed regarding this merged data are displayed. When there is no cross-check that has been determined as an error, the cross-check result displaying region D36 remains blank.

Figure 12:
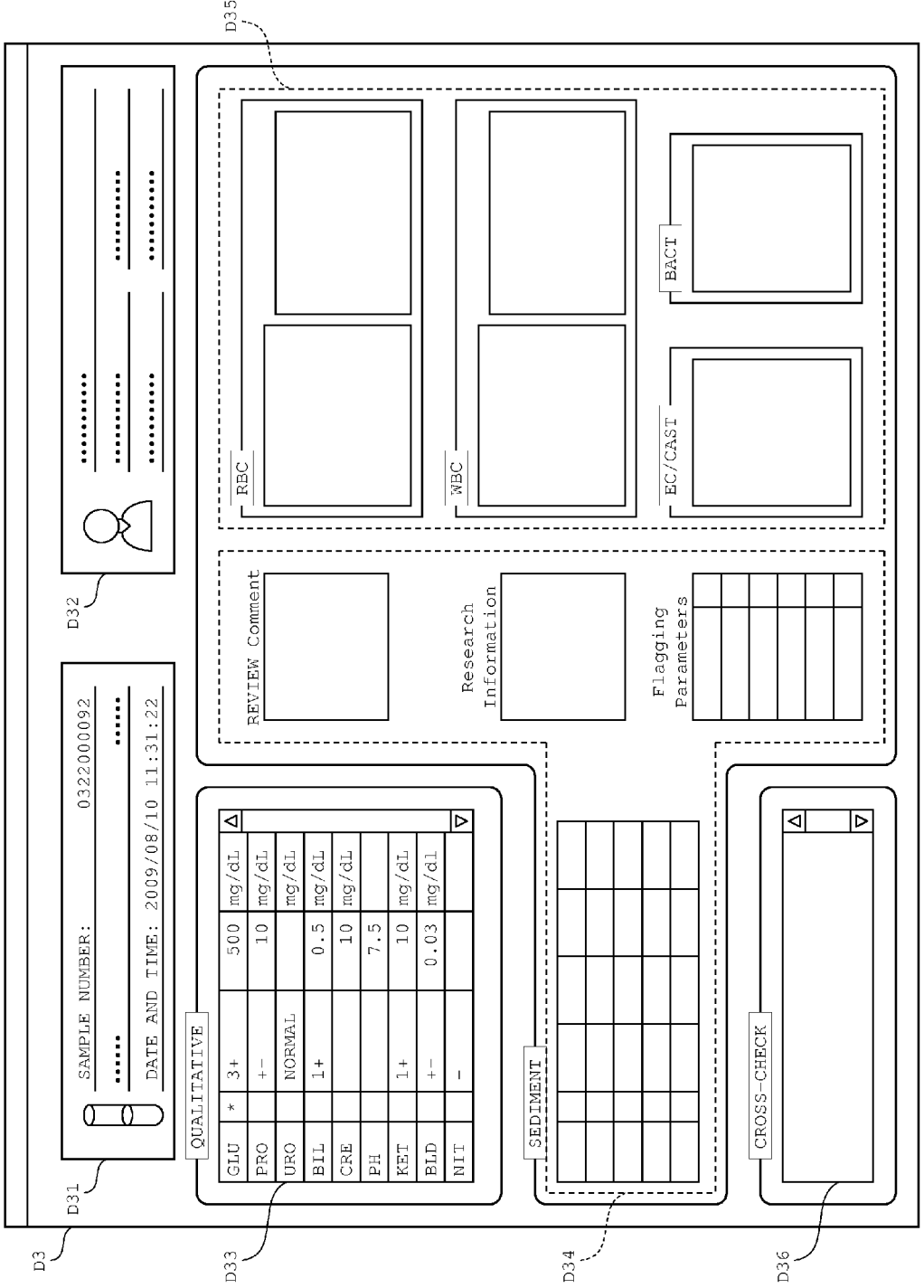
FIG. 12 shows a merged data displaying screen used when displaying merged data including only a qualitative measurement result according to an embodiment.

FIG. 12 shows the merged data displaying screen D3 when displaying merged data including only a qualitative measurement result. In the merged data displaying screen D3 shown in FIG. 12, merged data of the fourth line from the top of the list displaying region D21 shown in FIG. 10 is displayed.

Different from the merged data displaying screen D3 shown in FIG. 11, the merged data displaying screen D3 in this case does not include a sediment measurement result. Thus, the sediment measurement result displaying regions D34 and D35 are displayed in gray. In addition, the cross-check result displaying region D36 is also displayed in gray since no cross-check has been performed.

It should be noted that, when merged data including only a sediment measurement result is displayed, results of the sediment measurement are displayed in the sediment measurement result displaying regions D34 and D35, and the qualitative measurement result displaying region D33 and the cross-check result displaying region D36 are displayed in gray.

Figure 13:
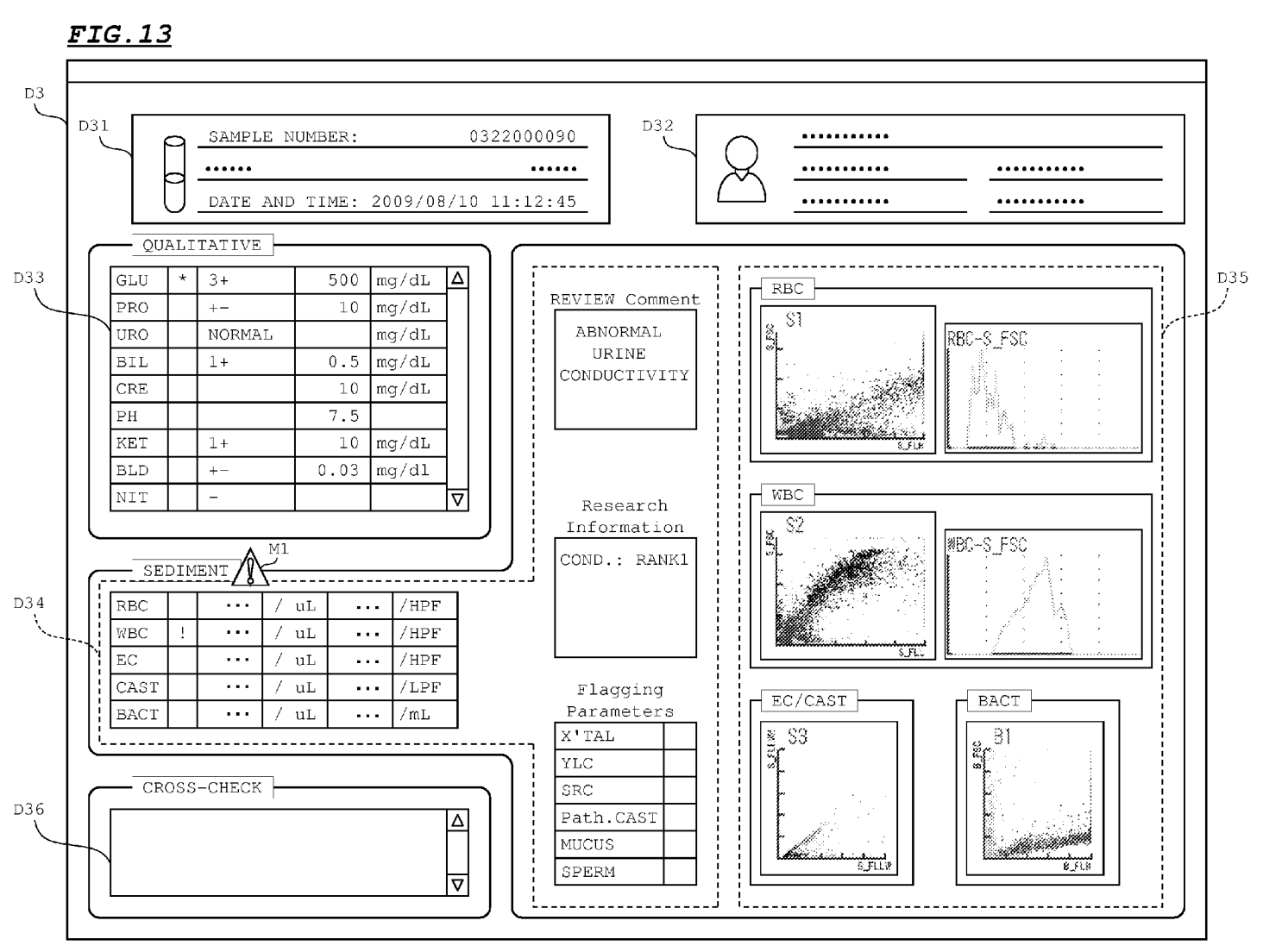

FIG. 13 shows the merged data displaying screen D3 when the elapsed time Tf from the qualitative measurement time to the sediment measurement time exceeds the set time period Ts. In the merged data displaying screen D3 shown in FIG. 13, merged data of the sixth line from the top of the list displaying region D21 shown in FIG. 10 is displayed.

In this case, with respect to the sediment measurement, the elapsed time Tf from the qualitative measurement time exceeds the set time period Ts. Thus, in the merged data displaying screen D3, an alarm symbol M1 indicating that the reliability of the sediment measurement result is low is displayed in the sediment measurement result displaying region D34, in addition to the regions included in the merged data displaying screen D3 shown in FIG. 11. At this time, results of the sediment measurement are displayed in the sediment measurement result displaying regions D34 and D35. Accordingly, based on the displayed results of the sediment measurement, the user can confirm the reliability of the measurement results, and can determine whether a retest is necessary for the sediment measurement. Thus, an unnecessary retest for the sediment measurement can be avoided. Further, in this case, since no cross-check has been performed, the cross-check result displaying region D36 is displayed in gray.

Figure 14:
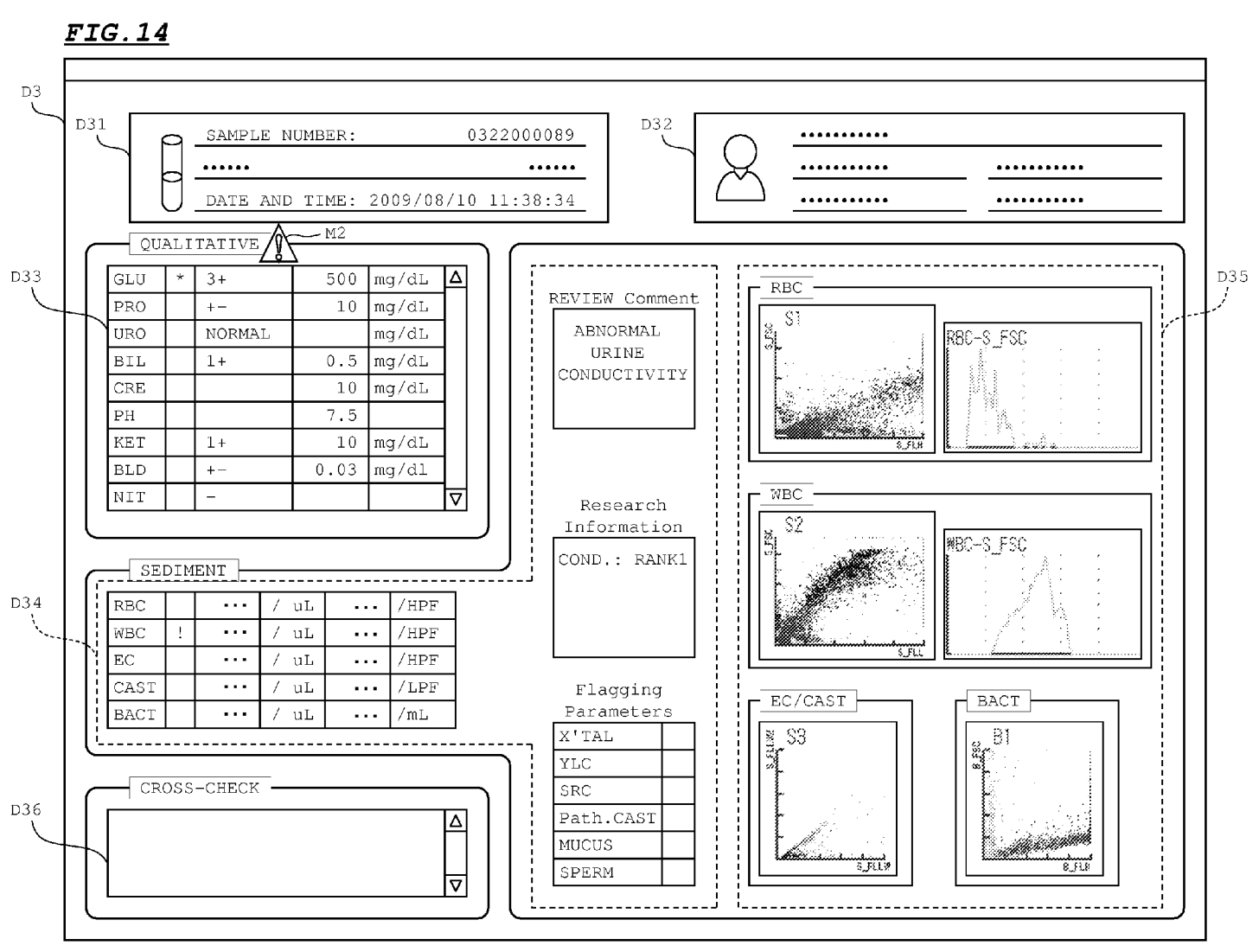

FIG. 14 shows the merged data displaying screen D3 when the elapsed time Tc from the sediment measurement time to the qualitative measurement time exceeds the set time period Ts. In the merged data displaying screen D3 shown in FIG. 14, merged data of the first line from the top of the list displaying region D21 shown in FIG. 10 is displayed.

In the merged data displaying screen D3 of this case, with respect to the qualitative measurement, the elapsed time Tc from the sediment measurement time exceeds the set time period Ts. Thus, an alarm symbol M2 indicating that the reliability of the qualitative measurement result is low is displayed in the qualitative measurement result displaying region D33, in addition to the regions included in the merged data displaying screen D3 shown in FIG. 11. Also in this case, as in the case of FIG. 13, results of the qualitative measurement are displayed in the qualitative measurement result displaying region D33. Since no cross-check has been performed, the cross-check result displaying region D36 is displayed in gray.

As described above, according to the present embodiment, when a sediment measurement result is obtained, if a qualitative measurement result having the same sample number has been stored in the qualitative measurement DB, it is determined whether the elapsed time Tf from the qualitative measurement time to the sediment measurement time exceeds the set time period Ts. When the elapsed time Tf exceeds the set time period Ts, the alarm symbol M1 is displayed in the sediment measurement result displaying regions D34 and D35 in the merged data displaying screen D3. Accordingly, the user can easily determine the reliability of the sediment measurement result based on the alarm symbol M1, without following the history of past qualitative measurements.

Similarly, when the elapsed time Tc from a sediment measurement time to a qualitative measurement time exceeds the set time period Ts, the alarm symbol M2 is displayed in the qualitative measurement result displaying region D33 in the merged data displaying screen D3. Accordingly, the user can easily determine the reliability of the qualitative measurement result based on the alarm symbol M2, without following the history of past sediment measurements.

Further, according to the present embodiment, even when the elapsed time Tf or Tc exceeds the set time period Ts, measurement results are displayed in the sediment measurement result displaying region D34 and D35 and the qualitative measurement result displaying region D33 in the merged data displaying screen D3. Accordingly, the user can confirm the reliability of the sediment or qualitative measurement result, and can determine whether a retest is necessary. Thus, an unnecessary retest can be avoided.

Further, according to the present embodiment, when the elapsed time Tf or Tc is shorter than the set time period Ts, a cross-check is performed based on the qualitative measurement result and the sediment measurement result. When the elapsed time Tf or Tc is longer than the set time period Ts, no cross-check is performed based on the qualitative measurement result and the sediment measurement result. Accordingly, it is possible to avoid a cross-check from being performed based on a measurement result whose reliability is relatively low.

Further, according to the present embodiment, the merged data displaying screen D3 simultaneously including qualitative and sediment measurement results of the same sample, and a cross-check result, and the alarm symbol M1 or M2 is displayed. Therefore, evaluation and examination of the qualitative measurement result and the sediment measurement result can be performed smoothly and efficiently.

Further, according to the present embodiment, the user can set the set time period Ts via the service setting screen D1. Therefore, compared with a case where the predetermined time period is fixed in advance, the degree of freedom for reliability determination can be increased.

An embodiment of the present invention has been described. However, the embodiment of the present invention is not limited thereto.

Figure 15:
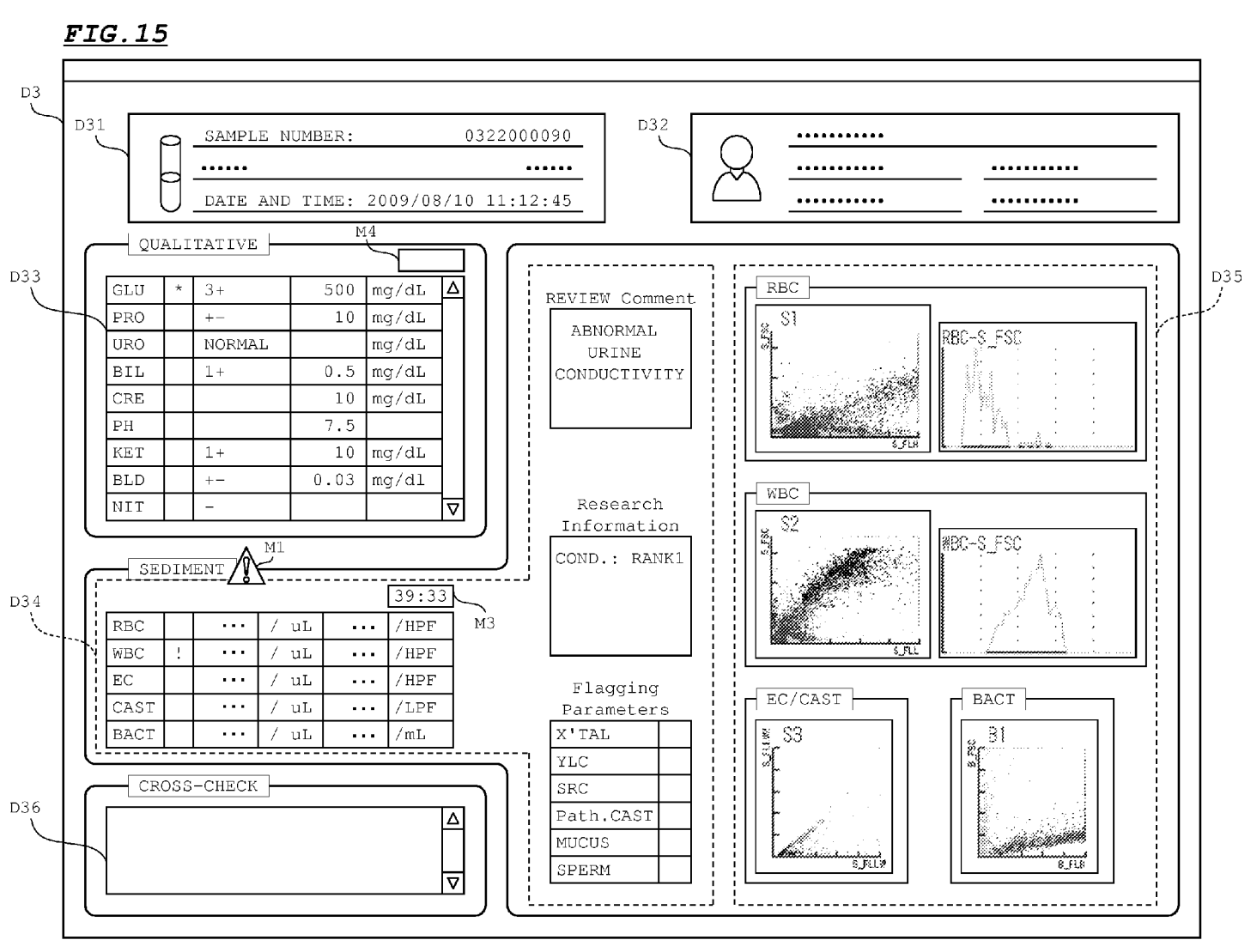

For example, in the above embodiment, when the elapsed time Tf or Tc exceeds the set time period Ts, the alarm symbol M1 or M2 is displayed in the merged data displaying screen D3. However, the elapsed time Tf or Tc may be additionally displayed in the merged data displaying screen D3. For example, as shown in FIG. 15, an elapsed time displaying region M3 may be further prepared in the sediment measurement result displaying region D34, and the elapsed time Tf may be displayed therein. Accordingly, the user can know the elapsed time from the qualitative measurement to the sediment measurement, and can determine the reliability of the sediment measurement result in a detailed manner.

It should be noted that, in this modification, the elapsed time displaying region M3 is displayed along with the alarm symbol M1. However, only the elapsed time displaying region M3 may be displayed.

Similarly, when the elapsed time Tc from the sediment measurement time to the qualitative measurement time exceeds the set time period Ts, an elapsed time displaying region M4 may be further prepared in the qualitative measurement result displaying region D33 in the merged data displaying screen D3, and the elapsed time Tc may be displayed therein. Similarly, the elapsed time displaying region M4 may be displayed along with the alarm symbol M2, or only the elapsed time displaying region M4 may be displayed.

Further, in the above embodiment, whether a measurement by the urine qualitative measurement part 10 is performed and whether a measurement by the urinary sediment measurement part 20 is performed are determined based on a qualitative measurement order and a sediment measurement order that are transmitted by the host computer 60, respectively. However, the present invention is not limited thereto. By the user performing an input onto the input section 410 (see FIG. 3) of the information processing apparatus 40, whether a measurement by the urine qualitative measurement part 10 is performed and whether a measurement by the urinary sediment measurement part 20 is performed may be determined without making an inquiry with the host computer 60.

Further, in the above embodiment, a subject to be measured is exemplified by urine, but a subject to be measured may be blood. That is, the present invention can also be applied to a sample analyzer which tests blood, and further, the present invention can be applied to a clinical sample analyzer which tests other clinical samples.

Further, in the above embodiment, the measurement by the urinary sediment measurement part 20 is performed by using a flow cytometer. However, the present invention is not limited thereto. The measurement by the urinary sediment measurement part 20 may be performed by an image of a urine sample being taken and the taken sediment image being analyzed. In this case, instead of the scattergrams displayed in the sediment measurement result displaying region D35 shown in FIG. 11 to FIG. 15, a sediment measurement result displaying region D35' (see FIG. 16) including such taken sediment images may be displayed. Further, the sediment measurement result displaying region D35' may be displayed along with the scattergrams displayed in the sediment measurement result displaying region D35 in FIG. 11 to FIG. 15. When the sediment measurement result displaying region D35' is displayed in this manner, the user can compare, with respect to the same sample, a combination of measurement results together with the sediment images, and thus, can more appropriately evaluate the measurement results of the sample.

Further, in the above embodiment, in the merged DB, the number in the number item of the qualitative measurement DB and the number in the number item of the sediment measurement DB are stored. However, the present invention is not limited thereto. A qualitative measurement result and a sediment measurement result that are combined together may be directly stored in the merged DB. Alternatively, in the merged DB, other information for identifying the measurement results, such as dates and times of the qualitative and sediment measurements to be combined together, may be stored.

Further, in the above embodiment, at the time of a sediment measurement and at the time of a qualitative measurement, the reliability of the measurement result is determined by using the same set time period Ts. However, different set time periods may be set for a sediment measurement and a qualitative measurement, respectively.

Further, in the above embodiment, when the elapsed time Tf from a qualitative measurement time to a sediment measurement time exceeds the set time period Ts, it is considered that the reliability of the sediment measurement result is low, and no cross-check is performed. However, thereafter, if the user determines that there is no problem with the reliability of the sediment measurement result based on the sediment measurement result and the elapsed time Tf from the qualitative measurement time, only a cross-check may be further performed using such a sediment measurement result.

Further, in the above embodiment, the time difference between a qualitative measurement and a sediment measurement is obtained by storing the measurement time of the qualitative measurement and the measurement time of the sediment measurement and calculating the difference therebetween. However, for each sample, a timer is started when a qualitative measurement is performed and the timer is stopped when a sediment measurement is performed, and the obtained time may be used as the time difference. It should be noted that, in this case, there may be a sample for which only a qualitative measurement is performed and no sediment measurement is performed. Therefore, in order to prevent the timer from continuing operation for such a sample, the timer may be automatically stopped when a predetermined time period, such as 24 hours, has elapsed.

It should be noted that, in the above embodiment, as the first measurement item and the second measurement item described in claims, "urine qualitative" measurement items and "urinary sediment" measurement items are used as examples. However, the first measurement item and the second measurement item described in claims are not limited thereto. For example, the first measurement item and the second measurement item described in claims may be an "urine qualitative" measurement item and a "urine qualitative" measurement item, or alternatively, a "urinary sediment" measurement item and a "urinary sediment" measurement item. Further, the first measurement item and the second measurement item described in claims may be a "biochemical" measurement item and an "immunological" measurement item.

In addition to the above, various modifications can be made as appropriate to the embodiment of the present invention without departing from the scope of the technical idea defined by the claims.

What is claimed is:

1. A sample analyzer comprising:
   a first measurement part which performs a measurement on a sample for a first measurement item;
   a second measurement part which performs a measurement on the sample for a second measurement item;
   an output section; and
   a controller which is programmed:
      to perform a cross-check between a first measurement result obtained by the first measurement part and a second measurement result obtained by the second measurement part, when a time difference between a measurement time of the measurement on the sample performed by the first measurement part and a measurement time of the measurement on the sample performed by the second measurement part is within a predetermined time period; and
      not to perform a cross-check between the first measurement result and the second measurement result when the time difference exceeds the predetermined time period.

2. The sample analyzer according to claim 1, wherein the first measurement item and the second measurement item are different from each other.

3. The sample analyzer according to claim 2, further comprising:
   a storage section configured to store the first measurement result and the second measurement result, wherein
   the controller performs a cross-check between the first measurement result and the second measurement result of a same sample stored in the storage section.

4. The sample analyzer according to claim 1, further comprising:
   a storage section configured to store the first measurement result and the second measurement result, wherein
   the first measurement part is a qualitative measurement part which performs a qualitative measurement on a urine sample for a urine qualitative measurement item,
   the second measurement part is a sediment measurement part which performs a sediment measurement on the urine sample for a urinary sediment measurement item,
   the storage section stores a qualitative measurement result obtained by the qualitative measurement part as the first measurement result and a sediment measurement result obtained by the sediment measurement part as the second measurement result, and
   the controller controls the output section to output, when a time difference between a measurement time of a measurement on a sample performed by the qualitative measurement part and a measurement time of a measurement on the sample performed by the sediment measurement part exceeds a predetermined time period, information indicating an alarm.

5. The sample analyzer according to claim 4, wherein the qualitative measurement and the sediment measurement are performed on a same sample, and
   the controller controls the output section to output, when the sediment measurement is performed later than the qualitative measurement and the time difference exceeds the predetermined time period, the information indicating an alarm.

6. The sample analyzer according to claim 5, wherein the controller controls the output section to output, when the time difference exceeds the predetermined time period, the sediment measurement result stored in the storage section along with the information indicating an alarm.

7. The sample analyzer according to claim 4, wherein the qualitative measurement and the sediment measurement are performed on a same sample,
   the controller controls the output section to output, when the qualitative measurement is performed later than the sediment measurement and the time difference exceeds the predetermined time period, the information indicating an alarm.

8. The sample analyzer according to claim 7, wherein when the time difference exceeds the predetermined time period, the controller controls the output section to output the qualitative measurement result stored in the storage section along with the information indicating an alarm.

9. The sample analyzer according to claim 4, wherein the output section includes a display section which displays a screen, and
   the controller controls the display section to display a screen including the qualitative measurement result and the sediment measurement result of the same sample, a result of the cross-check, and the information indicating an alarm.

10. The sample analyzer according to claim 1, further comprising:
    a setting section which sets the predetermined time period.

11. The sample analyzer according to claim 1, wherein the controller controls the output section to output the time difference as information indicating an alarm.

12. A sample analysis method for performing a measurement and an analysis of a sample, the sample analysis method comprising steps of:
    performing a first measurement on a sample for a first measurement item;
    performing a second measurement on the sample for a second measurement item;
    performing a cross-check between a first measurement result obtained by the first measurement part and a second measurement result obtained by the second measurement part, when a time difference between a measurement time of the measurement on the sample performed by the first measurement part and a measurement time of the measurement on the sample performed by the second measurement part is within a predetermined time period; and
    not performing a cross-check between the first measurement result and the second measurement result when the time difference exceeds the predetermined time period.

13. The sample analysis method according to claim 12, wherein
    the first measurement item and the second measurement item are different from each other.

14. The sample analysis method according to claim 13, further comprising steps of:
    storing the first measurement result;
    storing the second measurement result; and
    performing a cross-check between the first measurement result and the second measurement result of a same sample that are stored.

15. The sample analysis method according to claim 12, further comprising a step of:
    storing the first measurement result obtained in the first measurement step and the second measurement result obtained in the second measurement step, wherein
    a qualitative measurement on a urine sample for a urine qualitative measurement item is performed in the first measurement step, a sediment measurement on the urine sample for a urinary sediment measurement item is performed in the second measurement step, a qualitative measurement result obtained by the qualitative measurement and a sediment measurement result obtained by the sediment measurement are stored as the first measurement result and the second measurement result, respectively, in the storing step, and outputting, when a time difference between a measurement time of a qualitative measurement on a sample and a measurement time of a sediment measurement on the sample exceeds a predetermined time period, information indicating an alarm.

16. The sample analysis method according to claim 15, wherein the time difference is outputted as the information indicating an alarm in the outputting step.

17. A sample analyzer comprising:

a first measurement part which performs a measurement on a sample for a first measurement item;

a second measurement part which performs a measurement on the sample for a second measurement item;

an output section; and a controller programmed to:

perform a cross-check between a first measurement result obtained by the first measurement part and a second measurement result obtained by the second measurement part, when a time difference between a measurement time of a measurement on a sample performed by the first measurement part and a measurement time of a measurement on the sample performed by the second measurement part is within the predetermined time period; and control the output section to output, when the time difference exceeds a predetermined time period, information indicating an alarm.

18. The sample analyzer according to claim 17, wherein the first measurement item and the second measurement item are different from each other.

19. The sample analyzer according to claim 17, further comprising:

a storage section configured to store the first measurement result and the second measurement result, wherein the controller performs a cross-check between the first measurement result and the second measurement result of a same sample stored in the storage section.

20. The sample analyzer according to claim 17, wherein the controller controls the output section to output the time difference as the information indicating an alarm.

21. The sample analyzer according to claim 1, wherein the time period is set by a user, and is less than or equal to 60 minutes.

22. The sample analyzer according to claim 1, wherein when the time difference exceeds the predetermined time period, information is output indicating that the reliability of one of the first measurement result and the second measurement result is low.

* * * * *